(12) United States Patent
Cho et al.

(10) Patent No.: US 11,896,400 B2
(45) Date of Patent: Feb. 13, 2024

(54) ELECTRONIC DEVICE FOR UPDATING CALIBRATION DATA ON BASIS OF BLOOD PRESSURE INFORMATION, AND CONTROL METHOD

(71) Applicant: Samsung Electronics Co., Ltd., Gyeonggi-do (KR)

(72) Inventors: Sunghwan Cho, Gyeonggi-do (KR); Jinho Kim, Gyeonggi-do (KR); Seunghwan Shin, Gyeonggi-do (KR); Junseok Oh, Gyeonggi-do (KR); Inho Yun, Gyeonggi-do (KR); Hongji Lee, Gyeonggi-do (KR); Taehan Jeon, Gyeonggi-do (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 258 days.

(21) Appl. No.: 16/971,799

(22) PCT Filed: Feb. 13, 2019

(86) PCT No.: PCT/KR2019/001729
§ 371 (c)(1),
(2) Date: Aug. 21, 2020

(87) PCT Pub. No.: WO2019/164171
PCT Pub. Date: Aug. 29, 2019

(65) Prior Publication Data
US 2021/0030367 A1 Feb. 4, 2021

(30) Foreign Application Priority Data
Feb. 21, 2018 (KR) .................. 10-2018-0020820

(51) Int. Cl.
*A61B 5/00* (2006.01)
*A61B 5/024* (2006.01)
*A61B 5/021* (2006.01)

(52) U.S. Cl.
CPC .......... *A61B 5/7221* (2013.01); *A61B 5/0006* (2013.01); *A61B 5/02108* (2013.01);
(Continued)

(58) Field of Classification Search
CPC ... A61B 5/02108; A61B 5/021; A61B 5/0205; A61B 5/7235; A61B 5/02416; A61B 5/7475; G06F 16/436; A63B 5561/04
See application file for complete search history.

(56) References Cited

U.S. PATENT DOCUMENTS

| | | | |
|---|---|---|---|
| 2010/0081945 A1* | 4/2010 | Sethi ...................... | A61B 5/021 600/485 |
| 2015/0327785 A1 | 11/2015 | Lading et al. | |

(Continued)

FOREIGN PATENT DOCUMENTS

| | | |
|---|---|---|
| KR | 10-2011-0113140 A | 10/2011 |
| KR | 10-2013-0134052 A | 12/2013 |

(Continued)

OTHER PUBLICATIONS

Refaeilzadeh, Payam, Lei Tang, and Huan Liu. "Cross-validation." Encyclopedia of database systems 5 (2009): 532-538. (Year: 2009).*

(Continued)

*Primary Examiner* — Eric F Winakur
*Assistant Examiner* — Jonathan Drew Moroneso
(74) *Attorney, Agent, or Firm* — Cha & Reiter, LLC

(57) ABSTRACT

Provided are an electronic device for selectively storing blood pressure information and updating calibration data on the basis of the stored blood pressure information, and a control method. The electronic device comprises, a memory operably connected with the processor, wherein the memory can include instructions, during the execution thereof, for allowing the processor to, display a user interface on a display, allow the user interface to provide guidelines for measuring the blood pressure, receive first data from the motion sensor, receive second data from a PPG sensor, receive third data from the PPG sensor, determine the validity of the third data at least partially on basis of the first data and the second data, and display an indication on the (Continued)

user interface at least partially basis of the determined validity.

10 Claims, 22 Drawing Sheets

(52) U.S. Cl.
CPC ........ *A61B 5/02416* (2013.01); *A61B 5/6898* (2013.01); *A61B 5/7475* (2013.01); *A61B 5/742* (2013.01)

(56) References Cited

U.S. PATENT DOCUMENTS

| | | | |
|---|---|---|---|
| 2016/0029964 A1* | 2/2016 | LeBoeuf | A61B 5/6803 600/476 |
| 2016/0256117 A1 | 9/2016 | Baik et al. | |
| 2016/0302677 A1* | 10/2016 | He | A61B 5/1102 |
| 2017/0011210 A1* | 1/2017 | Cheong | A61B 5/681 |
| 2017/0042433 A1 | 2/2017 | Noh et al. | |
| 2018/0020917 A1* | 1/2018 | Lin | G06F 18/22 600/300 |
| 2018/0042486 A1* | 2/2018 | Yoshizawa | A61B 5/0077 |
| 2019/0104953 A1* | 4/2019 | Narasimhan | A61B 5/02225 |
| 2019/0142286 A1* | 5/2019 | Mouradian | A61B 5/6826 600/480 |

FOREIGN PATENT DOCUMENTS

| | | |
|---|---|---|
| KR | 10-2014-0003820 A | 1/2014 |
| KR | 10-2015-0057185 A | 5/2015 |
| KR | 10-2016-0107007 A | 9/2016 |
| KR | 10-2017-0019189 A | 2/2017 |

OTHER PUBLICATIONS

Korean Office Action dated Sep. 26, 2022.

* cited by examiner

ELECTRONIC DEVICE FOR UPDATING CALIBRATION DATA ON BASIS OF BLOOD PRESSURE INFORMATION, AND CONTROL METHOD

CROSS-REFERENCE TO RELATED APPLICATION(S)

This application is a National Phase Entry of PCT International Application No. PCT/KR2019/001729, which was filed on Feb. 13, 2019, and claims priority to Korean Patent Application No. 10-2018-0020820, which was filed on Feb. 21, 2018, the contents of which are incorporated herein by reference.

BACKGROUND

1. Field

The disclosure relates to an electronic device and control method of updating calibration data based on blood pressure information.

2. Description of the Related Art

More and more services and additional functions are being provided through electronic devices, e.g., smartphones, or other portable electronic devices. To meet the needs of various users and raise use efficiency of electronic devices, communication service carriers or device manufacturers are jumping into competitions to develop electronic devices with differentiated and diversified functionalities. Accordingly, various functions that are provided through electronic devices are evolving more and more.

SUMMARY

A cuff-less blood pressure measuring device, such as a smartphone, including a photoplethysmogram (PPG) sensor requires a calibration process on a PPG signal obtained by the PPG sensor to provide the user with an accurate blood pressure measurement based on the PPG signal. The calibration process may be performed using at least one piece of biometric information (e.g., PPG signal) (which may also be referred to herein as a "reference biometric signal," "reference PPG signal," "reference data," or "reference PPG data" for ease of description) obtained via a cuff-type blood pressure device. Accurate blood pressure information (e.g., systolic pressure, diastolic pressure, and heartrate) may be provided to the user via the calibration process. In performing the calibration process, the reference PPG signal may need to be updated (e.g., replaced) periodically (e.g., every week) or aperiodically. Such periodic or aperiodic update allows accurate blood pressure information to be provided to the user despite changes in the user's body. However, users of cuff-less blood pressure measuring devices may not be precisely aware of the update period of reference PPG signal. This may come from the fact that the period of maintaining the accuracy of calibration process may differ depending on the user's body state.

According to various embodiments of the disclosure, there is provided an electronic device that may selectively store (e.g., monitor) biometric information (e.g., blood pressure information) in a specific circumstance (e.g., a resting state) related to the user's body state and identify (e.g., determine) a trend of variations in the user's biometric information in the specific circumstance.

According to various embodiments of the disclosure, there is provided an electronic device that may update (e.g., change) reference biometric information (e.g., a reference PPG signal) for providing blood pressure information based on a trend of variations in biometric information in a specific circumstance.

According to various embodiments of the disclosure, an electronic device may comprise a housing, a touchscreen display exposed through a first portion of the housing, a motion sensor disposed inside the housing, a photoplethysmogram (PPG) sensor disposed in a second portion of the housing, a wireless communication circuit, a processor operatively connected with the display, the motion sensor, the PPG sensor, and the wireless communication circuit, and a memory operatively connected with the processor, wherein the memory stores instructions executed to enable the processor to display a user interface on the display, the user interface providing a guidance for blood pressure measurement, receive first data from the motion sensor and second data from the PPG sensor, receive third data from the PPG sensor, determine a validity of the third data based at least partially on the first data and the second data, and display an indication on the user interface based at least partially on the determined validity.

According to various embodiments of the disclosure, an electronic device may comprise a housing, a touchscreen display exposed through a first portion of the housing, a motion sensor disposed inside the housing, a photoplethysmogram (PPG) sensor disposed in a second portion of the housing, a wireless communication circuit, a processor operatively connected with the display, the motion sensor, the PPG sensor, and the wireless communication circuit, and a memory operatively connected with the processor, wherein the memory stores instructions executed to enable the processor to display a user interface on the display, the user interface providing a guidance for blood pressure measurement, receive first data from the PPG sensor, receive second data using the wireless communication circuit, the second data generated substantially simultaneously with the first data, and perform a calibration process on data from the PPG sensor based at least partially on the second data.

According to various embodiments of the disclosure, a method of operating an electronic device may comprise displaying a user interface on a display, the user interface providing a guidance for blood pressure measurement, receiving first data from a motion sensor of the electronic device and second data from a PPG sensor of the electronic device, and third data from the PPG sensor, determining a validity of the third data based at least partially on the first data and the second data, and displaying an indication on the user interface, based at least partially on the determined validity.

According to various embodiments of the disclosure, a method of operating an electronic device may comprise displaying a user interface on a display, the user interface providing a guidance for blood pressure measurement, receiving first data from a PPG sensor of the electronic device, receiving second data using a wireless communication circuit of the electronic device, the second data generated substantially simultaneously with the first data, and performing a calibration process on data from the PPG sensor, based at least partially on the second data.

According to various embodiments of the disclosure, it is possible to store (e.g., monitor) biometric information (e.g., blood pressure information) in a user's specific circumstance (e.g., a resting state), identifying (e.g., determining) a trend of variations in the user's biometric information in the specific circumstance.

According to various embodiments of the disclosure, it is possible to update reference biometric information (e.g., a reference PPG signal) for providing blood pressure information based on a trend of variations in biometric information in a specific circumstance, increasing the reliability of blood pressure information.

The effects set forth herein are not limited thereto, and it is apparent to one of ordinary skill in the art that various effects may be disclosed herein.

DETAILED DESCRIPTION

Figure 1:
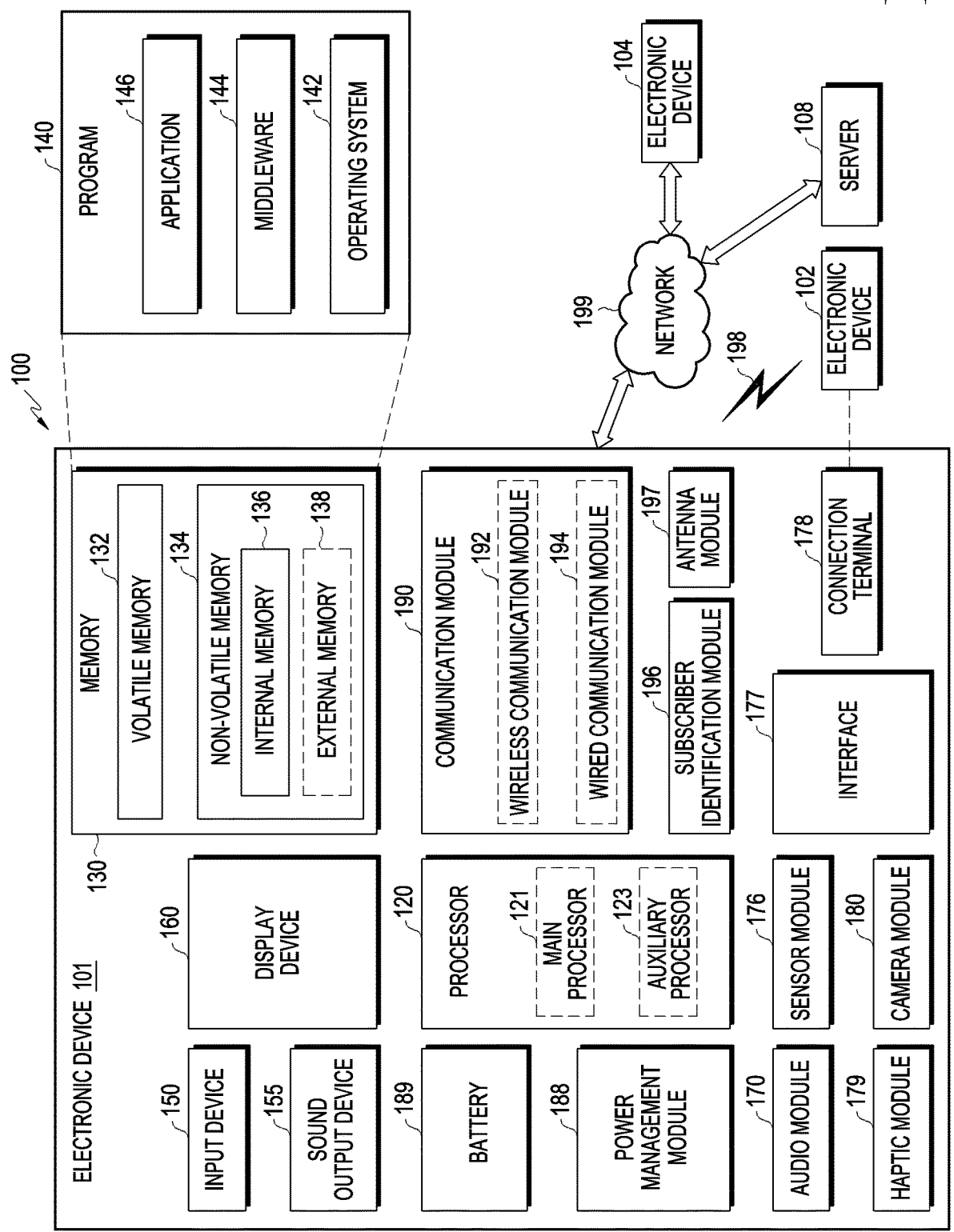
FIG. 1 is a view illustrating an electronic device in a network environment according to various embodiments.

FIG. 1 is a block diagram illustrating an electronic device 101 in a network environment 100 according to various embodiments. Referring to FIG. 1, the electronic device 101 in the network environment 100 may communicate with an electronic device 102 via a first network 198 (e.g., a short-range wireless communication network), or an electronic device 104 or a server 108 via a second network 199 (e.g., a long-range wireless communication network). According to an embodiment, the electronic device 101 may communicate with the electronic device 104 via the server 108. According to an embodiment, the electronic device 101 may include a processor 120, memory 130, an input device 150, a sound output device 155, a display device 160, an audio module 170, a sensor module 176, an interface 177, a haptic module 179, a camera module 180, a power management module 188, a battery 189, a communication module 190, a subscriber identification module (SIM) 196, or an antenna module 197. In some embodiments, at least one (e.g., the display device 160 or the camera module 180) of the components may be omitted from the electronic device 101, or one or more other components may be added in the electronic device 101. In some embodiments, some of the components may be implemented as single integrated circuitry. For example, the sensor module 176 (e.g., a fingerprint sensor, an iris sensor, or an illuminance sensor) may be implemented as embedded in the display device 160 (e.g., a display).

The processor 120 may execute, for example, software (e.g., a program 140) to control at least one other component (e.g., a hardware or software component) of the electronic device 101 coupled with the processor 120, and may perform various data processing or computation. According to one embodiment, as at least part of the data processing or computation, the processor 120 may load a command or data received from another component (e.g., the sensor module 176 or the communication module 190) in volatile memory 132, process the command or the data stored in the volatile memory 132, and store resulting data in non-volatile memory 134. According to an embodiment, the processor 120 may include a main processor 121 (e.g., a central processing unit (CPU) or an application processor (AP)), and an auxiliary processor 123 (e.g., a graphics processing unit (GPU), an image signal processor (ISP), a sensor hub processor, or a communication processor (CP)) that is operable independently from, or in conjunction with, the main processor 121. Additionally or alternatively, the auxiliary processor 123 may be adapted to consume less power than the main processor 121, or to be specific to a specified function. The auxiliary processor 123 may be implemented as separate from, or as part of the main processor 121.

The auxiliary processor 123 may control at least some of functions or states related to at least one component (e.g., the display device 160, the sensor module 176, or the communication module 190) among the components of the electronic device 101, instead of the main processor 121 while the main processor 121 is in an inactive (e.g., sleep) state, or together with the main processor 121 while the main processor 121 is in an active state (e.g., executing an application). According to an embodiment, the auxiliary processor 123 (e.g., an image signal processor or a communication processor) may be implemented as part of another component (e.g., the camera module 180 or the communication module 190) functionally related to the auxiliary processor 123.

The memory 130 may store various data used by at least one component (e.g., the processor 120 or the sensor module 176) of the electronic device 101. The various data may include, for example, software (e.g., the program 140) and input data or output data for a command related thereto. The memory 130 may include the volatile memory 132 or the non-volatile memory 134.

The program 140 may be stored in the memory 130 as software, and may include, for example, an operating system (OS) 142, middleware 144, or an application 146.

The input device 150 may receive a command or data to be used by other component (e.g., the processor 120) of the electronic device 101, from the outside (e.g., a user) of the electronic device 101. The input device 150 may include, for example, a microphone, a mouse, or a keyboard.

The sound output device 155 may output sound signals to the outside of the electronic device 101. The sound output device 155 may include, for example, a speaker or a receiver. The speaker may be used for general purposes, such as playing multimedia or playing record, and the receiver may be used for an incoming calls. According to an embodiment, the receiver may be implemented as separate from, or as part of the speaker.

The display device 160 may visually provide information to the outside (e.g., a user) of the electronic device 101. The display device 160 may include, for example, a display, a hologram device, or a projector and control circuitry to control a corresponding one of the display, hologram device, and projector. According to an embodiment, the display device 160 may include touch circuitry adapted to detect a touch, or sensor circuitry (e.g., a pressure sensor) adapted to measure the intensity of force incurred by the touch.

The audio module 170 may convert a sound into an electrical signal and vice versa. According to an embodiment, the audio module 170 may obtain the sound via the input device 150, or output the sound via the sound output device 155 or a headphone of an external electronic device (e.g., an electronic device 102) directly (e.g., wiredly) or wirelessly coupled with the electronic device 101.

The sensor module 176 may detect an operational state (e.g., power or temperature) of the electronic device 101 or an environmental state (e.g., a state of a user) external to the electronic device 101, and then generate an electrical signal or data value corresponding to the detected state. According to an embodiment, the sensor module 176 may include, for example, a gesture sensor, a gyro sensor, an atmospheric pressure sensor, a magnetic sensor, an acceleration sensor, a grip sensor, a proximity sensor, a color sensor, an infrared (IR) sensor, a biometric sensor, a temperature sensor, a humidity sensor, or an illuminance sensor.

The interface 177 may support one or more specified protocols to be used for the electronic device 101 to be coupled with the external electronic device (e.g., the electronic device 102) directly (e.g., wiredly) or wirelessly. According to an embodiment, the interface 177 may include, for example, a high definition multimedia interface (HDMI), a universal serial bus (USB) interface, a secure digital (SD) card interface, or an audio interface.

A connecting terminal 178 may include a connector via which the electronic device 101 may be physically connected with the external electronic device (e.g., the electronic device 102). According to an embodiment, the connecting terminal 178 may include, for example, a HDMI connector, a USB connector, a SD card connector, or an audio connector (e.g., a headphone connector).

The haptic module 179 may convert an electrical signal into a mechanical stimulus (e.g., a vibration or motion) or electrical stimulus which may be recognized by a user via his tactile sensation or kinesthetic sensation. According to an embodiment, the haptic module 179 may include, for example, a motor, a piezoelectric element, or an electric stimulator.

The camera module 180 may capture a still image or moving images. According to an embodiment, the camera module 180 may include one or more lenses, image sensors, image signal processors, or flashes.

The power management module 188 may manage power supplied to the electronic device 101. According to one embodiment, the power management module 188 may be implemented as at least part of, for example, a power management integrated circuit (PMIC).

The battery 189 may supply power to at least one component of the electronic device 101. According to an embodiment, the battery 189 may include, for example, a primary cell which is not rechargeable, a secondary cell which is rechargeable, or a fuel cell.

The communication module 190 may support establishing a direct (e.g., wired) communication channel or a wireless communication channel between the electronic device 101 and the external electronic device (e.g., the electronic device 102, the electronic device 104, or the server 108) and performing communication via the established communication channel. The communication module 190 may include one or more communication processors that are operable independently from the processor 120 (e.g., the application processor (AP)) and supports a direct (e.g., wired) communication or a wireless communication. According to an embodiment, the communication module 190 may include a wireless communication module 192 (e.g., a cellular communication module, a short-range wireless communication module, or a global navigation satellite system (GNSS) communication module) or a wired communication module 194 (e.g., a local area network (LAN) communication module or a power line communication (PLC) module).

A corresponding one of these communication modules may communicate with the external electronic device via the first network 198 (e.g., a short-range communication network, such as BLUETOOTH™, wireless-fidelity (Wi-Fi) direct, or infrared data association (IrDA)) or the second network 199 (e.g., a long-range communication network, such as a cellular network, the Internet, or a computer network (e.g., LAN or wide area network (WAN)). These various types of communication modules may be implemented as a single component (e.g., a single chip), or may be implemented as multi components (e.g., multi chips) separate from each other. The wireless communication module 192 may identify and authenticate the electronic device 101 in a communication network, such as the first network 198 or the second network 199, using subscriber information (e.g., international mobile subscriber identity (IMSI)) stored in the subscriber identification module 196.

The antenna module 197 may transmit or receive a signal or power to or from the outside (e.g., the external electronic device). According to an embodiment, the antenna module 197 may include one or more antennas, and, therefrom, at least one antenna appropriate for a communication scheme used in the communication network, such as the first network 198 or the second network 199, may be selected, for example, by the communication module 190 (e.g., the wireless communication module 192). The signal or the power may then be transmitted or received between the communication module 190 and the external electronic device via the selected at least one antenna.

At least some of the above-described components may be coupled mutually and communicate signals (e.g., commands or data) therebetween via an inter-peripheral communication scheme (e.g., a bus, general purpose input and output (GPIO), serial peripheral interface (SPI), or mobile industry processor interface (MIPI)).

According to an embodiment, commands or data may be transmitted or received between the electronic device 101 and the external electronic device 104 via the server 108 coupled with the second network 199. Each of the electronic devices 102 and 104 may be a device of a same type as, or a different type, from the electronic device 101. According to an embodiment, all or some of operations to be executed at the electronic device 101 may be executed at one or more of the external electronic devices 102, 104, or 108. For example, if the electronic device 101 should perform a function or a service automatically, or in response to a request from a user or another device, the electronic device 101, instead of, or in addition to, executing the function or the service, may request the one or more external electronic devices to perform at least part of the function or the service. The one or more external electronic devices receiving the request may perform the at least part of the function or the service requested, or an additional function or an additional service related to the request, and transfer an outcome of the performing to the electronic device 101. The electronic device 101 may provide the outcome, with or without further processing of the outcome, as at least part of a reply to the request. To that end, a cloud computing, distributed computing, or client-server computing technology may be used, for example.

Figure 2A:
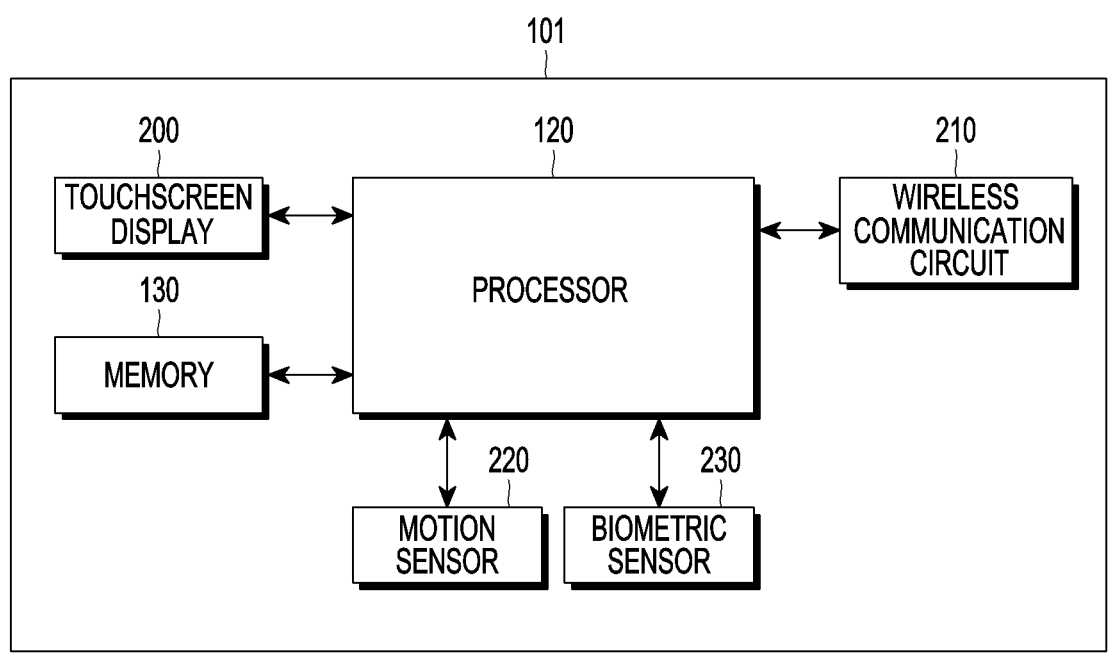
FIG. 2A is a view illustrating an example for describing an electronic device according to various embodiments.

FIG. 2A is a view illustrating an example for describing an electronic device 101 (e.g., the electronic device 101 of FIG. 1) according to various embodiments.

Referring to FIG. 2A, an electronic device 101 according to various embodiments of the disclosure may include a processor 120 (e.g., the processor 120 of FIG. 1), a memory 130 (e.g., the memory 130 of FIG. 1), a touchscreen display 200, a wireless communication circuit 210, a motion sensor 220, and/or a biometric sensor 230.

According to various embodiments of the disclosure, the processor 120 may execute software (e.g., the program 140 of FIG. 1) to control at least one other component (e.g., the memory 130, the touchscreen display 200, the wireless communication circuit 210, the motion sensor 220, and/or the biometric sensor 230) connected to the processor 120 and may perform various types of data processing or computation. According to various embodiments of the disclosure, the processor 120 may process various signals obtained from the biometric sensor 230 (e.g., a PPG sensor). For example, according to various embodiments of the disclosure, the processor 120 may process PPG signals provided from the biometric sensor 230 (e.g., a PPG sensor). According to various embodiments of the disclosure, the processor 120 may process PPG signals based on a pulse wave analysis (PWA) scheme. According to various embodiments of the disclosure, the processor 120 may identify the user's blood pressure information (e.g., systolic pressure and diastolic pressure) from a PPG signal. According to various embodiments of the disclosure, the biometric sensor 230 may identify the user's blood pressure information (e.g., systolic pressure and diastolic pressure) based on a pulse wave velocity (PWV) scheme. According to various embodiments of the disclosure, the biometric sensor 230 may further include at least one sensor (e.g., at least one electrode) for obtaining electrocardiogram (ECG) signals, in addition to the PPG sensor, to obtain the user's blood pressure information based on the PWV scheme. According to various embodiments of the disclosure, the processor 120 may identify the user's blood pressure information (e.g., systolic pressure and diastolic pressure) based on a PPG sensor and a sensor for obtaining ECG signals.

According to various embodiments of the disclosure, the processor 120 may identify the heartrate and/or peak-to-peak interval (PPI)-related information (e.g., time interval) (which may be simply referred to herein as "PPI information" for ease of description) from the PPG signal obtained from the biometric sensor 230. According to various embodiments of the disclosure, various techniques may be used in a method for measuring the heartrate and/or PPI information from the PPG signal obtained by the processor 120 from the biometric sensor 230. According to various embodiments of the disclosure, the processor 120 may determine the user's stress level (e.g., stress index) based on, at least, the measured heartrate or PPI information. According to various embodiments of the disclosure, if the electronic device 101 includes ECG electrodes, the stress level may be identified using R-R interval (RRI) information obtained using an ECG signal.

According to various embodiments of the disclosure, the processor 120 may use a PPG signal for calibration (which may be referred to herein as a "reference PPG signal") to identify the user's blood pressure information. According to various embodiments of the disclosure, the reference PPG signal may be stored in the electronic device (e.g., the memory 130 of FIG. 1). According to various embodiments of the disclosure, the reference PPG signal may include one or more PPG signals. According to various embodiments of the disclosure, the electronic device (e.g., the memory 130 of FIG. 1) may store blood pressure information corresponding to each of one or more reference PPG signals. For example, according to various embodiments of the disclosure, the electronic device (e.g., the memory 130 of FIG. 1) may store information about the waveform characteristics (e.g., peak value of PPG signal (e.g., pulse wave) and peak-to-peak time gap) of PPG signals. According to various embodiments of the disclosure, the processor 120 may identify the characteristics of the biometric signal (e.g., PPG signal) (which may be referred to herein as a "target biometric signal" or "target PPG signal" or in other various terms for ease of description) obtained to measure the biometric information (e.g., blood pressure). According to various embodiments of the disclosure, the processor 120 may identify the characteristics (e.g., peak characteristics) of the target PPG signal by second-order differentiating the target PPG signal. According to various embodiments of the disclosure, the processor 120 may compare the characteristics of the target PPG signal with the characteristics of the reference PPG signal, estimating the user's current blood pressure.

According to various embodiments of the disclosure, the reference data may include at least one PPG signal and at least one piece of blood pressure information (e.g., systolic pressure value and diastolic pressure value) corresponding to at least one PPG signal. In this case, to identify (e.g., estimate) blood pressure information from the target PPG signal, e.g., displacements of feature points and blood pressure variations corresponding to the feature point displacements may be stored in the form of a lookup table (LUT). According to various embodiments of the disclosure, the processor 120 may identify the displacement of at least one feature point of the target PPG signal and reference PPG signal and obtain the user's blood pressure information based on the information stored in the lookup table. Or, according to various embodiments of the disclosure, the blood pressure variation corresponding to the displacement of at least one feature point may be preset. According to various embodiments of the disclosure, the processor 120 may identify the displacement of at least one feature point of the target PPG signal and reference PPG signal and apply the preset blood pressure variation, corresponding to the identified displacement, to the reference PPG signal, thereby measuring the user's blood pressure. According to various embodiments of the disclosure, the reference PPG signal may include a plurality of PPG signals and blood pressure information corresponding to each of the plurality of PPG signals. In this case, according to various embodiments of the disclosure, the processor 120 may obtain the user's blood pressure information from the obtained target PPG signal using, e.g., an interpolation method. According to various embodiments of the disclosure, there may be applied various techniques that measure the user's blood pressure using the reference PPG signal and the target PPG signal.

According to various embodiments of the disclosure, the processor 120 may obtain the user's blood pressure information based on a PWV scheme. In this case, according to various embodiments of the disclosure, the electronic device 101 may include at least one electrode for obtaining ECG signals. According to various embodiments of the disclosure, the processor 120 may obtain an image of an area around the user's face using an imaging device (e.g., a normal camera or an IR camera) and identify variations in blood flow based on changes in the color of the user's face included in the obtained image. According to various embodiments of the disclosure, the processor 120 may also determine the arrival time of blood flow (pulse transit time) required in the PWV scheme, based on the identified variation in blood flow. According to various embodiments of the disclosure, the processor 120 may also calculate the pulse transit time required in the PWV scheme by measuring balistocardiogram (BCG) using an acceleration sensor.

According to various embodiments of the disclosure, the memory 130 may store various data used by at least one component (e.g., the processor 120, the motion sensor 220, or the biometric sensor 230) of the electronic device 101.

According to various embodiments of the disclosure, the touchscreen display 200 may visually provide information to the outside (e.g., the user) of the electronic device 101. According to various embodiments of the disclosure, the touchscreen display 200 may include touch circuitry adapted to detect a touch, or sensor circuitry (e.g., a pressure sensor) adapted to measure the intensity of force incurred by the touch.

According to various embodiments of the disclosure, the wireless communication circuit 210 may establish a wireless communication channel between the electronic device and an external electronic device (e.g., the electronic device 102 of FIG. 1, the electronic device 104 of FIG. 1, or the server 108 of FIG. 1) and support communication via the established wireless communication channel. According to various embodiments of the disclosure, the wireless communication circuit 210 may receive various data (e.g., biometric information) from an external electronic device (e.g., the electronic device 102 of FIG. 1, the electronic device 104 of FIG. 1, or the server 108 of FIG. 1).

According to various embodiments of the disclosure, the motion sensor 220 may sense an operation state (e.g., motion) of the electronic device 101 and generate an electrical signal or data value corresponding to the sensed state. According to various embodiments of the disclosure, the motion sensor 220 may include an acceleration sensor. According to various embodiments of the disclosure, the motion sensor 220 may include various sensors capable of sensing the motion of the electronic device 101.

According to various embodiments of the disclosure, the biometric sensor 230 may sense (e.g., obtain) the user's biometric information. According to various embodiments of the disclosure, the biometric information may include cardiovascular information, such as arterial stiffness, blood pressure, arterial age, PPI information, RRI information, heart rate, and/or oxygen saturation. According to various embodiments of the disclosure, the biometric sensor 230 may include at least one light source (e.g., an LED) with various wavelengths for obtaining biometric information. According to various embodiments of the disclosure, the biometric sensor 230 may include a PPG sensor. According to various embodiments of the disclosure, the biometric sensor 230 (e.g., a PPG sensor) may obtain a PPG signal. The PPG signal may be obtained as the biometric sensor 230 (e.g., a PPG sensor), according to various embodiments of the disclosure, detects a fluctuation in the optical signal corresponding to a variation in the volume of blood vessels. The PPG signal may mean a signal obtained based on the correlation between the fluctuation in optical signal and the variation in the volume of blood vessels.

Figure 2B:
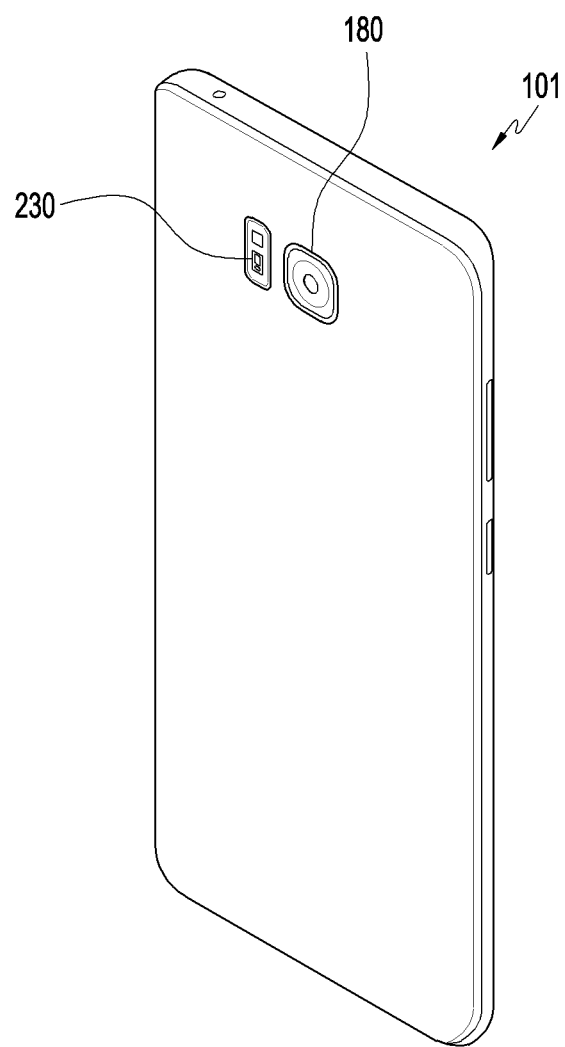
FIGS. 2B and 2C are views illustrating an example in which an electronic device with a biometric sensor is disposed according to various embodiments.
Figure 2C:
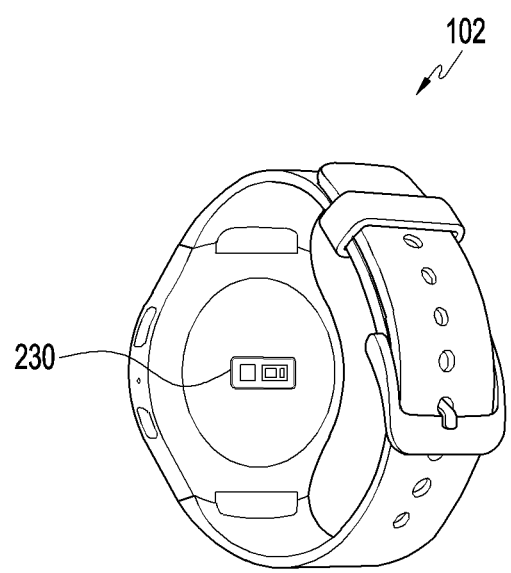

FIGS. 2B and 2C are views illustrating an example in which an electronic device with a biometric sensor is disposed according to various embodiments.

Referring to FIG. 2B, according to various embodiments of the disclosure, the electronic device 101 may be implemented as a smartphone. According to various embodiments of the disclosure, the biometric sensor 230 may be disposed on the back surface (e.g., the surface facing away from the surface where the display is disposed) of the electronic device 101 (e.g., a smartphone). According to various embodiments of the disclosure, the biometric sensor 230 may be disposed adjacent to a camera module 180 (e.g., the camera module 180 of FIG. 1) on the back surface (e.g., the surface facing away from the surface where the display is disposed) of the electronic device 101 (e.g., a smartphone).

Referring to FIG. 2C, according to various embodiments of the disclosure, the electronic device 101 may be implemented as a wearable device (e.g., a smart watch). According to various embodiments of the disclosure, the biometric sensor 230 may be disposed on the back surface (e.g., the surface facing away from the surface where the display is disposed) of the electronic device 101 (e.g., a wearable device).

According to various embodiments of the disclosure, the biometric sensor (e.g., the biometric sensor 230 of FIG. 2A) may be disposed in a first portion of the housing of the electronic device 101.

Figure 2D:
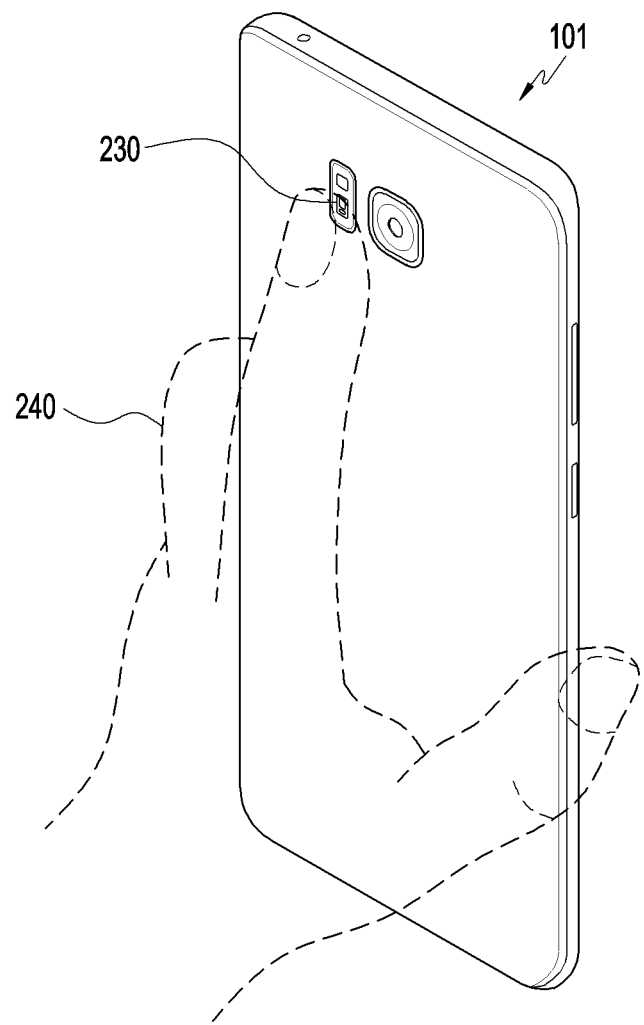
FIG. 2D is a view illustrating an example method of obtaining biometric information via a biometric sensor of an electronic device according to various embodiments.

FIG. 2D is a view illustrating an example method of obtaining biometric information via a biometric sensor of an electronic device according to various embodiments.

Referring to FIG. 2D, according to various embodiments of the disclosure, the biometric information or signal for identifying the biometric information may be obtained as a body portion (e.g., the user's finger) of the user 240 touches or approaches the biometric sensor 230. According to various embodiments of the disclosure, the biometric information or signal for identifying the biometric information may be obtained in various manners depending on the position where the biometric sensor 230 is placed in the electronic device 101.

Figure 3A:
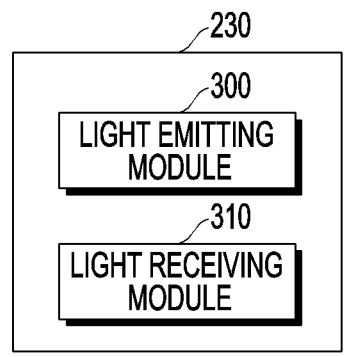
FIGS. 3A and 3B are views illustrating an example for describing a biometric sensor according to various embodiments.
Figure 3B:
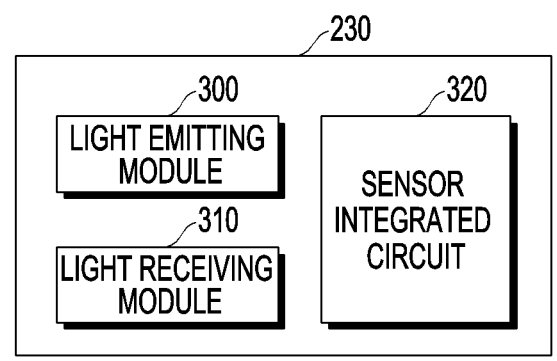

FIGS. 3A and 3B are views illustrating an example for describing a biometric sensor 230 (e.g., the biometric sensor 230 of FIG. 2A) according to various embodiments.

Referring to FIG. 3A, according to various embodiments of the disclosure, the biometric sensor 230 (e.g., a PPG sensor) may include a light emitting module 300 and a light receiving module 310.

According to various embodiments of the disclosure, the light emitting module 300 may output light to the outside to generate (e.g., obtain) a biometric signal (e.g., a PPG signal). According to various embodiments of the disclosure, the light emitting module 300 may include at least one of a vertical cavity surface emitting laser (VCSEL), a light emitting diode (LED), a white LED, and a white laser. According to various embodiments of the disclosure, the light emitting module 300 may include various light sources to output various wavelength ranges of light (e.g., blue, green, red, and/or infrared (IR)). According to various embodiments of the disclosure, the electronic device (e.g., the electronic device 101 of FIG. 1) may obtain a PPG signal using at least one of the various light sources. According to various embodiments of the disclosure, the light emitting module 300 may output light modulated to have a specific frequency so as to generate a PPG signal.

According to various embodiments of the disclosure, the light receiving module 310 may receive the light output from the light emitting module 300 and reflected by an object (e.g., the user). According to various embodiments of the disclosure, the light receiving module 310 may convert the received light into an electrical signal. According to various embodiments of the disclosure, the light receiving module 310 may generate a PPG signal using the received light. According to various embodiments of the disclosure, the light receiving module 310 may include at least one of an avalanche photodiode (APD), a single photon avalanche diode (SPAD), a photodiode, a photomultiplier tube (PMT), a charge-coupled device (CCD), a complementary metal-oxide-semiconductor (CMOS) array, or a spectrometer. According to various embodiments of the disclosure, the light emitting module 300 may include various light sources to output various wavelength ranges of light.

Referring to FIG. 3B, according to various embodiments of the disclosure, the biometric sensor 230 (e.g., a PPG sensor) may include a light emitting module 300, a light receiving module 310, and a sensor integrated circuit 320.

According to various embodiments of the disclosure, the sensor integrated circuit 320 may perform at least some functions performed by a processor (e.g., the processor 120 of FIG. 2A). According to various embodiments of the disclosure, the sensor integrated circuit 320, together with at least one module of the light emitting module 300 and the light receiving module 310, may be implemented as a single chip. According to various embodiments of the disclosure, the sensor integrated circuit 320 may be implemented as a separate module from the light emitting module 300 and the light receiving module 310 and be connected to be operable with the light emitting module 300 and the light receiving module 310. According to various embodiments of the disclosure, the description made in connection with FIG. 3A may apply likewise to the light emitting module 300 and the light receiving module 310.

Figure 4:
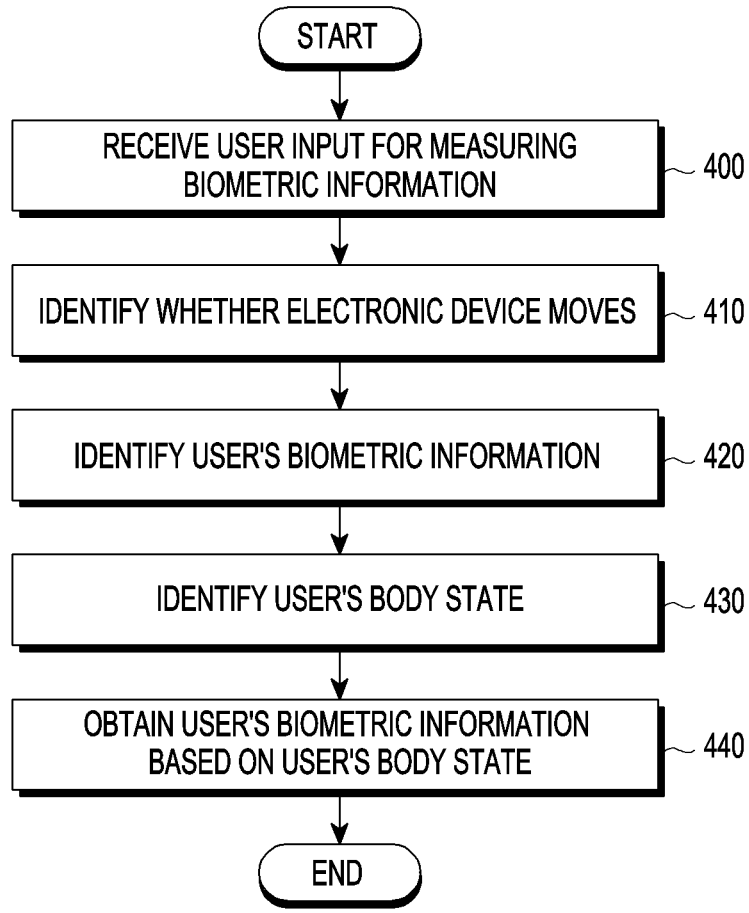
FIG. 4 is a view illustrating an example method of operating an electronic device according to various embodiments.

FIG. 4 is a view illustrating an example method of operating an electronic device (e.g., the electronic device 101 of FIG. 2A) according to various embodiments.

Referring to FIG. 4, according to various embodiments of the disclosure, in a method of operating an electronic device (e.g., the electronic device 101 of FIG. 2A), the electronic device (e.g., the processor 120 of FIG. 2A) may receive a user input for measuring biometric information (e.g., blood pressure) in operation 400.

According to various embodiments of the disclosure, the user input may include, e.g., the user's selection input for a blood pressure measurement item on a specific application (e.g., healthcare related application such as SAMSUNG HEALTH™ application)

According to various embodiments of the disclosure, in the method of operating an electronic device (e.g., the electronic device 101 of FIG. 2A), the electronic device (e.g., the processor 120 of FIG. 2A) may identify whether the electronic device (e.g., the electronic device 101 of FIG. 2A) moves, using a motion sensor (e.g., the motion sensor 220 of FIG. 2A) in operation 410. According to various embodiments of the disclosure, the electronic device (e.g., the processor 120 of FIG. 2A) may identify whether the electronic device (e.g., the electronic device 101 of FIG. 2A) moves, based on motion information (e.g., acceleration) about the electronic device (e.g., the electronic device 101 of FIG. 2A), detected by the motion sensor (e.g., the motion sensor 220 of FIG. 2A). According to various embodiments of the disclosure, the electronic device (e.g., the processor 120 of FIG. 2A) may identify that the electronic device (e.g., the electronic device 101 of FIG. 2A) has moved if the motion information (e.g., acceleration) exceeds a designated range (or a designated threshold). According to various embodiments of the disclosure, various techniques may be applied to identify the motion of the electronic device (e.g., the electronic device 101 of FIG. 2A).

According to various embodiments of the disclosure, in the method of operating an electronic device (e.g., the electronic device 101 of FIG. 2A), the electronic device (e.g., the processor 120 of FIG. 2A) may identify the user's biometric information using a biometric sensor (e.g., the biometric sensor 230 of FIG. 2A) in operation 420. Operation 420 may be carried out in the manner shown in FIG. 2D, as an example. According to various embodiments of the disclosure, the biometric information may include at least one of heartrate and PPI information. According to various embodiments of the disclosure, the biometric information may further include various pieces information other than heartrate and PPI information. According to various embodiments of the disclosure, the electronic device (e.g., the processor 120 of FIG. 2A) may identify the user's stress level (which is the stress index represented as high, normal, and low) using at least one of the heartrate and PPI information. According to various embodiments of the disclosure, the electronic device (e.g., the memory 130 of FIG. 1) may previously store, in a lookup table, information containing the correlation between stress index and biometric information (e.g., at least one of heartrate and PPI information (or RRI information)). According to various embodiments of the disclosure, the electronic device (e.g., the processor 120 of FIG. 2A) may obtain the user's biometric information according to operation 420 and identify the user's stress level (e.g., stress index) based on the lookup table. According to various embodiments of the disclosure, various techniques may be applied to the method of identifying the stress index using the PPI information.

According to various embodiments of the disclosure, in the method of operating an electronic device (e.g., the electronic device 101 of FIG. 2A), the electronic device (e.g., the processor 120 of FIG. 2A) may identify the user's body state in operation 430. According to various embodiments of the disclosure, the electronic device (e.g., the processor 120 of FIG. 2A) may identify that the user is currently in a stable state if at least part of the biometric information obtained according to operation 420 does not exceed a designated range (or a designated threshold). According to various embodiments of the disclosure, if at least part of the biometric information obtained according to operation 420 is not less than the designated range, the electronic device (e.g., the processor 120 of FIG. 2A) may identify that the user is currently in an unstable state (e.g., while the user is moving or immediately after the user's motion has been done). According to various embodiments of the disclosure, the electronic device (e.g., the processor 120 of FIG. 2A) may identify the user's state (e.g., the stable state or unstable state) based on the user's stress index.

According to various embodiments of the disclosure, if the stress index indicates a first designated state (e.g., a "normal" state and/or "low" state), the electronic device (e.g., the processor 120 of FIG. 2A) may identify that the user is currently in the stable state. According to various embodiments of the disclosure, if the stress index indicates a second designated state (e.g., a "high" state), the electronic device (e.g., the processor 120 of FIG. 2A) may identify that the user is currently in the unstable state. According to various embodiments of the disclosure, upon identifying that no motion is detected from the electronic device (e.g., the electronic device 101 of FIG. 2A) according to operation 410 and that the user's state is the stable state according to operation 420, the electronic device (e.g., the processor 120 of FIG. 2A) may identify that the user's current body state is a resting state. Or, according to various embodiments of the disclosure, upon identifying that no motion is detected from the electronic device (e.g., the electronic device 101 of FIG. 2A) according to operation 410 but that the user's state is the unstable state according to operation 420, the electronic device (e.g., the processor 120 of FIG. 2A) may identify that the user's current body state is an active state.

According to various embodiments of the disclosure, in the method of operating an electronic device (e.g., the electronic device 101 of FIG. 2A), the electronic device (e.g., the processor 120 of FIG. 2A) may obtain the user's biometric information (e.g., blood pressure information) (e.g., measure blood pressure) based on the user's body state identified according to operation 430, using the biometric sensor (e.g., the biometric sensor 230 of FIG. 2A) in operation 440. According to various embodiments of the disclosure, upon identifying that the user's body state identified according to operation 430 is the resting state, the electronic device (e.g., the processor 120 of FIG. 2A) may perform a process for measuring the user's blood pressure. According to various embodiments of the disclosure, upon identifying that the user's body state identified according to operation 430 is the active state, the electronic device (e.g., the processor 120 of FIG. 2A) may refrain from measuring the user's blood pressure. In this case, a user interface indicating that the process for measuring blood pressure is not performed may be displayed on the electronic device (e.g., the display device 160 of FIG. 1). Or, the user may be notified of it via various auditory or visual effects. According to various embodiments of the disclosure, upon identifying that the user's body state identified according to operation 430 is the active state, the electronic device (e.g., the processor 120 of FIG. 2A) may measure the user's blood pressure and store the measured blood pressure in the electronic device (e.g., the memory 130 of FIG. 1). In this case, according to various embodiments of the disclosure, the electronic device (e.g., the processor 120 of FIG. 2A) may not store the measured blood pressure as blood pressure in resting state. According to various embodiments of the disclosure, upon providing the user with the blood pressure information not stored as blood pressure in resting state (e.g., information in active state), the electronic device (e.g., the processor 120 of FIG. 2A) may provide a notification message indicating that the state of the measured blood pressure may be inaccurate because it is not the blood pressure in resting state, along with the blood pressure information. According to various embodiments of the disclosure, the blood pressure information may include at least one of systolic pressure, diastolic pressure, and heartrate. According to various embodiments of the disclosure, the blood pressure information may be obtained based on a PPG signal generated by the biometric sensor (e.g., the biometric sensor 230 of FIG. 2A).

For ease of description of various embodiments of the disclosure, it may be assumed that the user may keep the user's body portion (e.g., the user's finger) in contact or close to the biometric sensor (e.g., the biometric sensor 230 of FIG. 2A) while performing operations 420 to 440 or operations 410 to 440.

According to various embodiments of the disclosure, at least one operation shown in FIG. 4 may be omitted or combined with other operation(s), or the order of operations may be changed or the operations may be modified in various manners and be performed. According to various embodiments of the disclosure, at least one operation shown in FIG. 4 may be performed simultaneously or at different times.

Figure 5A:
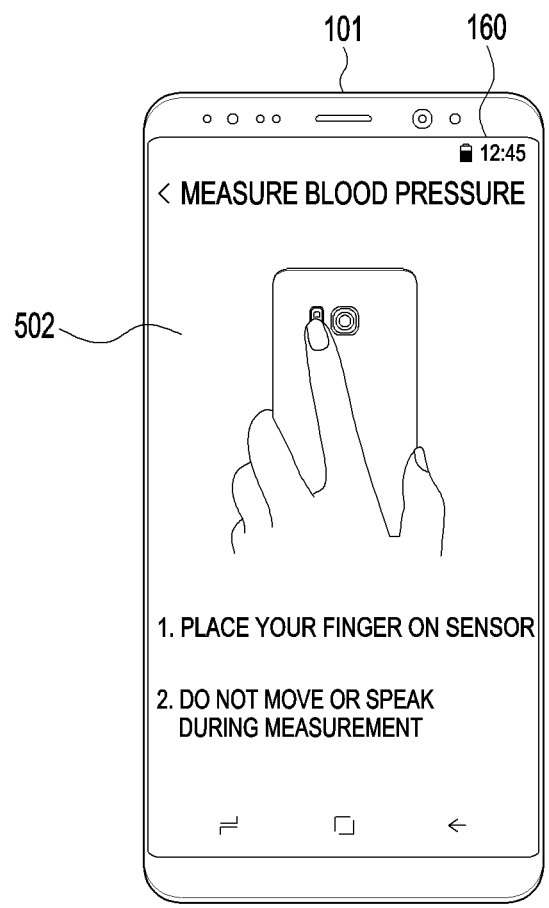
FIGS. 5A, 5B and 5C are views illustrating an example for describing the operation of providing a user with a guidance for obtaining the user's biometric information (e.g., blood pressure) according to various embodiments.
Figure 5B:
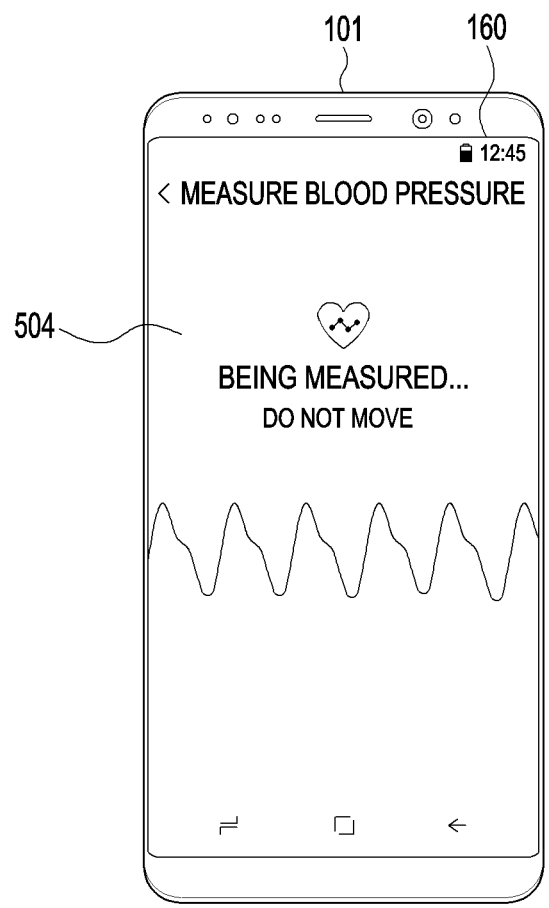
Figure 5C:
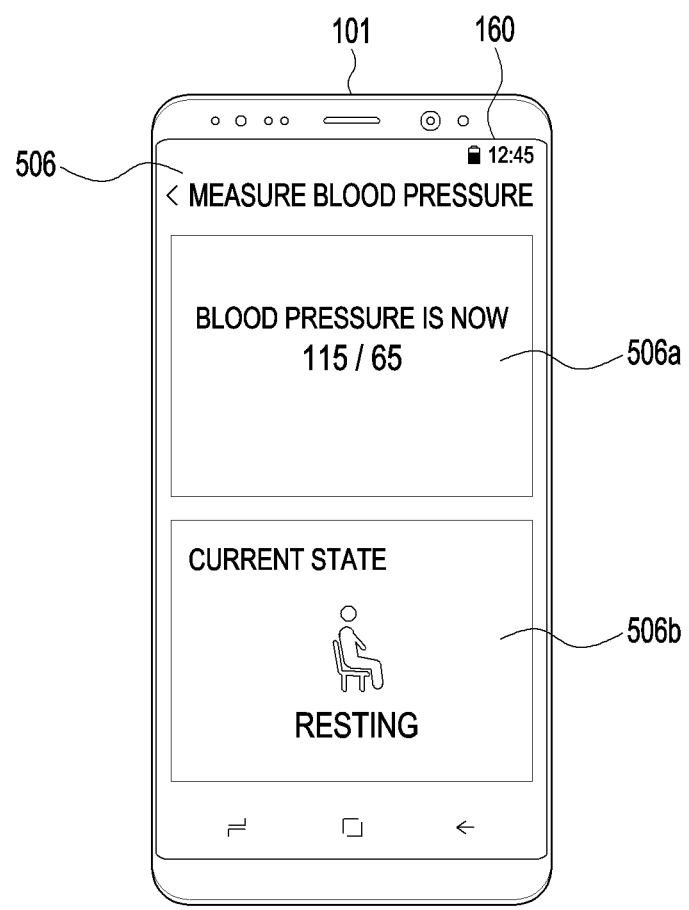

FIGS. 5A to 5C are views illustrating an example for describing the operation of providing a user with a guidance for obtaining the user's biometric information (e.g., blood pressure) according to various embodiments.

Referring to FIG. 5A, according to various embodiments of the disclosure, the electronic device 101 (e.g., the electronic device 101 of FIG. 2A) may display a first screen 502, including a guidance for measuring blood pressure, on the display device 160 (e.g., the touchscreen display 200 of FIG. 2A). According to various embodiments of the disclosure, upon receiving a user input for measuring biometric information (e.g., blood pressure) from the user, the electronic device 101 may display the first screen 502 on the display device 160.

Referring to FIG. 5B, according to various embodiments of the disclosure, if the user touches the biometric sensor (e.g., the biometric sensor 230 of FIG. 2A) with the user's finger, the electronic device 101 may display a second screen 504, including a notification indicating that blood pressure is being measured, on the display device 160. According to various embodiments of the disclosure, upon performing a process for obtaining the user's biometric information (e.g., operations 420 and 430 of FIG. 4), the electronic device 101 may display the second screen 504 on the display device 160.

Referring to FIG. 5C, according to various embodiments of the disclosure, if measurement of blood pressure is done, the electronic device 101 may display a third screen 506, including the result 506a of blood pressure measurement and/or a notification 506b related to the user's current body state (e.g., resting state or active state), on the display device 160. According to various embodiments of the disclosure, after storing the obtained biometric information in the electronic device (e.g., the memory 130 of FIG. 1) (e.g., operation 440 of FIG. 4), the electronic device 101 may display the third screen 506 on the display device 160.

Figure 6:
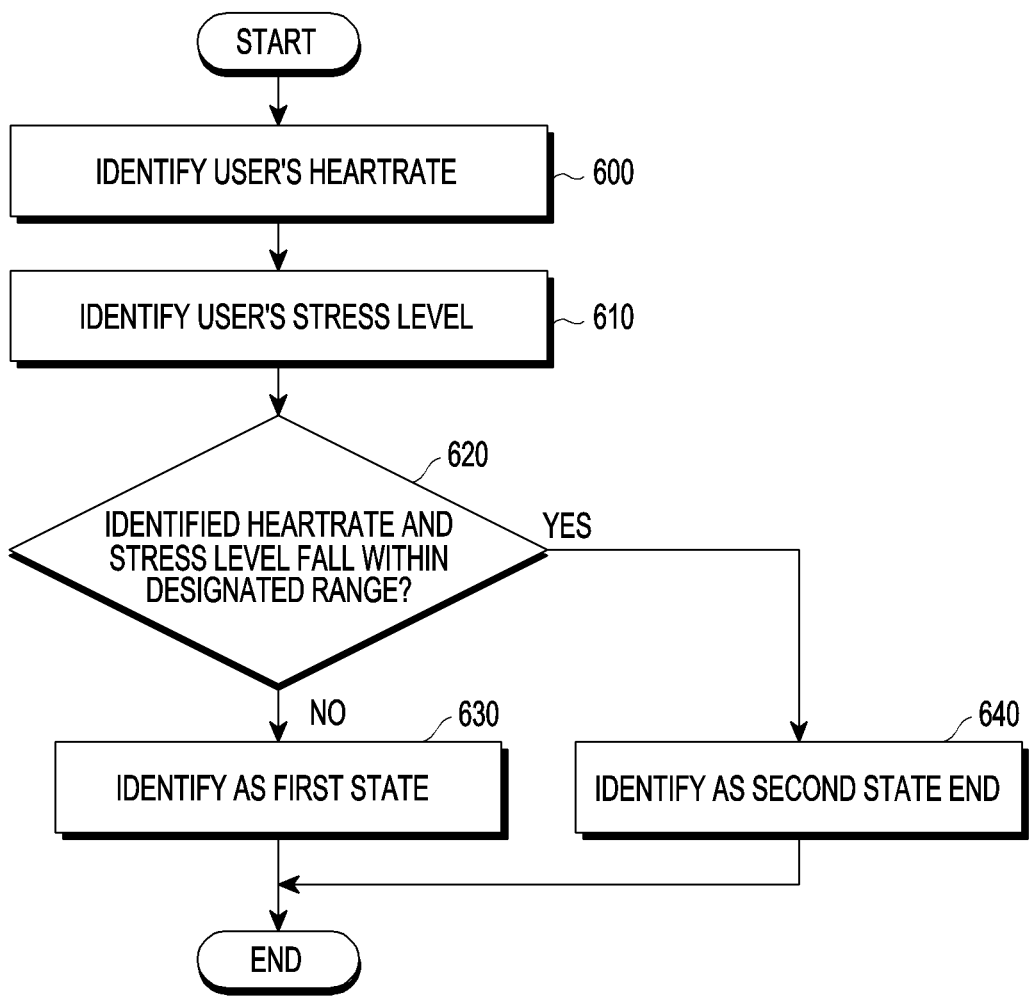
FIGS. 6 and 7 are views illustrating an example method of operating an electronic device according to various embodiments.

FIG. 6 is a view illustrating an example method of operating an electronic device (e.g., the electronic device 101 of FIG. 2A) according to various embodiments. FIG. 6 illustrates example operations for identifying the user's biometric information in connection with operation 420 of FIG. 4, according to various embodiments of the disclosure.

Referring to FIG. 6, according to various embodiments of the disclosure, in the method of operating an electronic device (e.g., the electronic device 101 of FIG. 2A), the electronic device (e.g., the processor 120 of FIG. 2A) may identify the user's heartrate using a biometric sensor (e.g., the biometric sensor 230 of FIG. 2A) in operation 600. According to various embodiments of the disclosure, the electronic device (e.g., the processor 120 of FIG. 2A) may identify the heartrate based on a PPG signal or using other various techniques. According to various embodiments of the disclosure, the electronic device (e.g., the light emitting module 300 of FIG. 3A) may output light with at least one wavelength for identifying the user's heartrate.

According to various embodiments of the disclosure, in the method of operating an electronic device (e.g., the electronic device 101 of FIG. 2A), the electronic device (e.g., the processor 120 of FIG. 2A) may identify the user's stress level in operation 610. According to various embodiments of the disclosure, the electronic device (e.g., the processor 120 of FIG. 2A) may identify the user's stress level (e.g., stress index) using the user's heartrate and/or PPI information (or RRI information).

Referring to FIG. 6, according to various embodiments of the disclosure, in the method of operating the electronic device (e.g., the electronic device 101 of FIG. 2A), the electronic device (e.g., the processor 120 of FIG. 2A) may identify whether the identified heartrate and/or stress level falls within a designated range (e.g., when the currently identified heartrate has been 10 bpm to 20 bpm increased as compared to the heartrate identified at a specific time (e.g., the heartrate identified immediately before) and when the stress level is "high") in operation 620.

Referring to FIG. 6, according to various embodiments of the disclosure, in the method of operating the electronic device (e.g., the electronic device 101 of FIG. 2A), unless the identified heartrate and/or stress level falls within the designated range, the electronic device (e.g., the processor 120 of FIG. 2A) may identify that the user's current state body is a first state (e.g., the stable state (or resting state)) in operation 630.

Referring to FIG. 6, according to various embodiments of the disclosure, in the method of operating the electronic device (e.g., the electronic device 101 of FIG. 2A), if the identified heartrate and/or stress level falls within the designated range, the electronic device (e.g., the processor 120 of FIG. 2A) may identify that the user's current state body is a second state (e.g., the unstable state (or active state)) in operation 640.

According to various embodiments of the disclosure, at least one operation shown in FIG. 6 may be omitted or combined with other operation(s), or the order of operations may be changed or the operations may be modified in various manners and be performed. According to various embodiments of the disclosure, at least one operation shown in FIG. 6 may be performed simultaneously or at different times. Although various embodiments of the disclosure have been described with "heartrate" and "PPI information" in connection with FIG. 6 for ease of description, other biometric information may be additionally/interchangeably applied. In the disclosure, the blood pressure measured in the resting state may be referred to as a "resting blood pressure" for ease of description. According to various embodiments of the disclosure, the electronic device (e.g., the processor 120 of FIG. 2A) may determine that the blood pressure determined to be the "resting blood pressure" is a blood pressure with validity.

Figure 7:
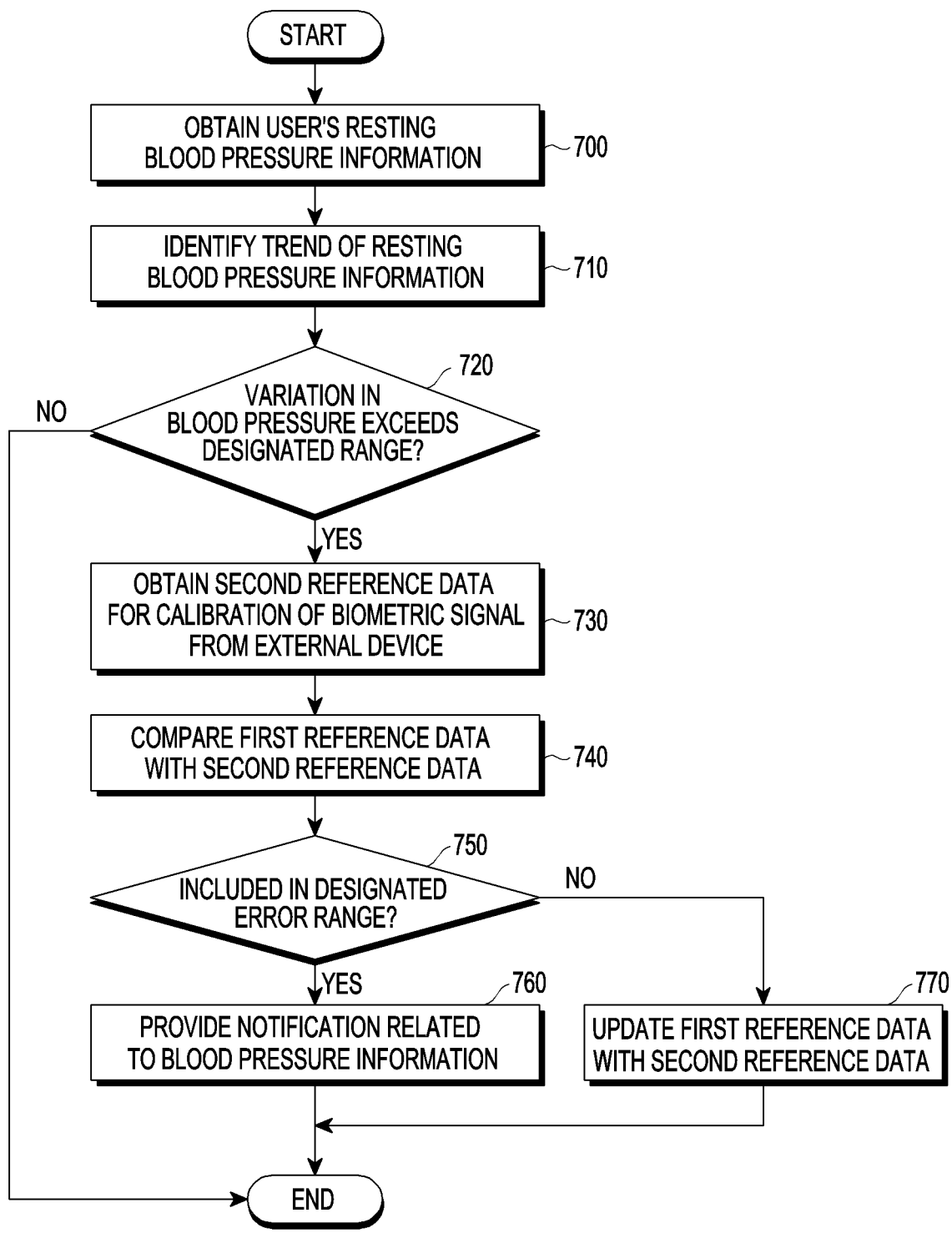

FIG. 7 is a view illustrating an example method of operating an electronic device (e.g., the electronic device 101 of FIG. 2A) according to various embodiments. There is described in connection with FIG. 7 an embodiment in which the electronic device (e.g., the processor 120 of FIG. 2A) determines whether reference data is updated (e.g., changed) depending on the trend of resting blood pressure.

Referring to FIG. 7, according to various embodiments of the disclosure, a method of operating the electronic device (e.g., the electronic device 101 of FIG. 2A) may include the operation of the electronic device (e.g., the processor 120 of FIG. 2A) obtaining (e.g., storing) the user's resting blood pressure information in operation 700. According to various embodiments of the disclosure, the electronic device (e.g., the electronic device 101 of FIG. 2A) may obtain the user's resting blood pressure information according to, e.g., the operations of FIG. 4.

According to various embodiments of the disclosure, the method of operating the electronic device (e.g., the electronic device 101 of FIG. 2A) may include the operation of the electronic device (e.g., the processor 120 of FIG. 2A) identifying the trend of resting blood pressure information in operation 710. According to various embodiments of the disclosure, the electronic device (e.g., the electronic device 101 of FIG. 2A) may identify the trend of variations in systolic pressure and/or diastolic pressure, a designated number of times or during a designated period.

According to various embodiments of the disclosure, in the method of operating the electronic device (e.g., the electronic device 101 of FIG. 2A), the electronic device (e.g., the processor 120 of FIG. 2A) may identify whether the variation in blood pressure exceeds (or is not less than) a designated range (e.g., a designated threshold) as a result of identifying the trend according to operation 710, in operation 720. For example, in a case where the designated range is 0% to 3%, if the trend of variations in resting blood pressure (e.g., the increase rate of systolic blood pressure) from the blood pressure value (e.g., systolic pressure) obtained at the time when the resting blood pressure was first obtained or a time before the designated period (e.g., one month) to a specific time (e.g., the latest time when blood pressure was measured) has a variation exceeding 3% (e.g., when the slope of the trend of systolic pressure exceeds 3%), the electronic device (e.g., the processor 120 of FIG. 2A) according to various embodiments of the disclosure may determine that comparison is needed between the reference data currently stored in the electronic device (e.g., the memory 130 of FIG. 1) and new reference data. In other words, according to various embodiments of the disclosure, the electronic device (e.g., the processor 120 of FIG. 2A) may compare each piece of data to identify whether the variation in blood pressure comes from the user's health problem or a reduction in calibration reliability due to a change in the user's body state (i.e., arrival of the time of updating the reference data). According to various embodiments of the disclosure, the electronic device (e.g., the processor 120 of FIG. 2A) may determine whether comparison with new reference data is required based on whether the standard deviation (or variance) of blood pressure data (e.g., systolic blood pressure value) obtained a designated number of times (or during a designated period) exceeds a designated value (e.g., 2).

According to various embodiments of the disclosure, the method of operating the electronic device (e.g., the electronic device 101 of FIG. 2A) may include the operation of the electronic device (e.g., the processor 120 of FIG. 2A) obtaining second reference data (e.g., a PPG signal and/or information about systolic pressure and diastolic pressure) for calibration of biometric signal in operation 730. According to various embodiments of the disclosure, the method may include the operation of the electronic device (e.g., the electronic device 101 of FIG. 2A) obtaining the second reference data for calibration of biometric signal from an external device (e.g., a cuff-type blood pressure device) connected with the electronic device (e.g., the electronic device 101 of FIG. 2A) via wireless or wired communication. According to various embodiments of the disclosure, the electronic device (e.g., the electronic device 101 of FIG. 2A) may directly receive information about systolic pressure and diastolic pressure from the user. In this case, to obtain information about the PPG signal (e.g., the waveform of PPG signal) corresponding to the received systolic pressure and diastolic pressure, the PPG signal may be obtained using a biometric sensor (e.g., the biometric sensor 230 of FIG. 2A). According to various embodiments of the disclosure, upon receiving the systolic pressure and diastolic pressure, the electronic device (e.g., the electronic device 101 of FIG. 2A) may display a user interface (e.g., "Place your finger on the sensor") to guide to allow a body portion (e.g., a finger) to contact the biometric sensor (e.g., the biometric sensor 230 of FIG. 2A). According to various embodiments of the disclosure, the electronic device (e.g., the electronic device 101 of FIG. 2A) may receive the second reference data from an external electronic device (e.g., a cloud server).

According to various embodiments of the disclosure, in the method of operating the electronic device (e.g., the electronic device 101 of FIG. 2A), the electronic device (e.g., the processor 120 of FIG. 2A) may compare the first reference data (e.g., a first PPG signal) with the second reference data (e.g., a second PPG signal) in operation 740. According to various embodiments of the disclosure, the first reference data may mean data that the electronic device (e.g., the processor 120 of FIG. 2A) is currently using for calibration. According to various embodiments of the disclosure, the second reference data may mean data for calibration, which the electronic device (e.g., the processor 120 of FIG. 2A) has newly obtained in operation 730. According to various embodiments of the disclosure, the operation of the electronic device (e.g., the processor 120 of FIG. 2A) comparing the first reference data (e.g., the first PPG signal) with the second reference data (e.g., the second PPG signal) is described in connection with FIGS. 9A and 9B.

According to various embodiments of the disclosure, in the method of operating the electronic device (e.g., the electronic device 101 of FIG. 2A), the electronic device (e.g., the processor 120 of FIG. 2A) may identify whether the result of data comparison according to operation 740 falls within a designated error range in operation 750. According to various embodiments of the disclosure, if the result of data comparison according to operation 740 falls within the designated error range, the electronic device (e.g., the processor 120 of FIG. 2A) may determine that calibration does not need to update. According to various embodiments of the disclosure, if the result of data comparison according to operation 740 exceeds the designated error range, the electronic device (e.g., the processor 120 of FIG. 2A) may determine that calibration needs to update. In operation 750, according to various embodiments of the disclosure, the electronic device (e.g., the processor 120 of FIG. 2A) may determine whether at least one of the systolic pressure and diastolic pressure exceeds a designated error range. According to various embodiments of the disclosure, if at least one of the systolic pressure and diastolic pressure exceeds the designated error range, the electronic device (e.g., the processor 120 of FIG. 2A) may determine that the designated error range has been exceeded.

According to various embodiments of the disclosure, in the method of operating the electronic device (e.g., the electronic device 101 of FIG. 2A), if the result of comparison according to operation 740 falls within the designated error range, the electronic device (e.g., the processor 120 of FIG. 2A) may provide a notification related to blood pressure information in operation 760. If the result of comparison according to operation 740 falls within the designated error range, this may mean that the reference data does not need to update, i.e., that the reliability for the blood pressure estimated by the electronic device (e.g., the processor 120 of FIG. 2A), according to various embodiments of the disclosure, is maintained. In other words, if the result of data comparison according to operation 740 falls within the designated error range, this may mean that such an extent of change as to need to be identified by the user occurs in the user's body. Thus, according to various embodiments of the disclosure, the electronic device (e.g., the processor 120 of FIG. 2A) may provide the user with a blood pressure information-related notification (e.g., an alert message indicating that the blood pressure has steadily risen), motivating the user to check up on the user's health condition.

According to various embodiments of the disclosure, in the method of operating the electronic device (e.g., the electronic device 101 of FIG. 2A), unless the result of comparison according to operation 740 falls within the designated error range, the electronic device (e.g., the processor 120 of FIG. 2A) may update the first reference data with the second reference data in operation 770. Unless the result of data comparison according to operation 740 falls within the designated error range, this may mean that the reference data needs to update, i.e., that the reliability for the blood pressure estimated by the electronic device (e.g., the processor 120 of FIG. 2A), according to various embodiments of the disclosure, has decreased. In this case, according to various embodiments of the disclosure, the electronic device (e.g., the processor 120 of FIG. 2A) may update the first reference data with the second reference data and use data more appropriate for the user's current body state as data for calibration. Thus, according to various embodiments of the disclosure, the electronic device (e.g., the processor 120 of FIG. 2A) may provide the user with more reliable blood pressure information.

The method of operating the electronic device according to various embodiments of the disclosure, shown in FIG. 7 may be triggered or performed at various times, e.g., a designated time after the resting blood pressure has been obtained, when the resting blood pressure is obtained a designated number of times, or when the time designated by the user arrives. According to various embodiments of the disclosure, at least one operation shown in FIG. 7 may be omitted or combined with other operation(s), or the order of operations may be changed or the operations may be modified in various manners and be performed. According to various embodiments of the disclosure, at least one operation shown in FIG. 7 may be performed simultaneously or at different times.

Figure 8A:
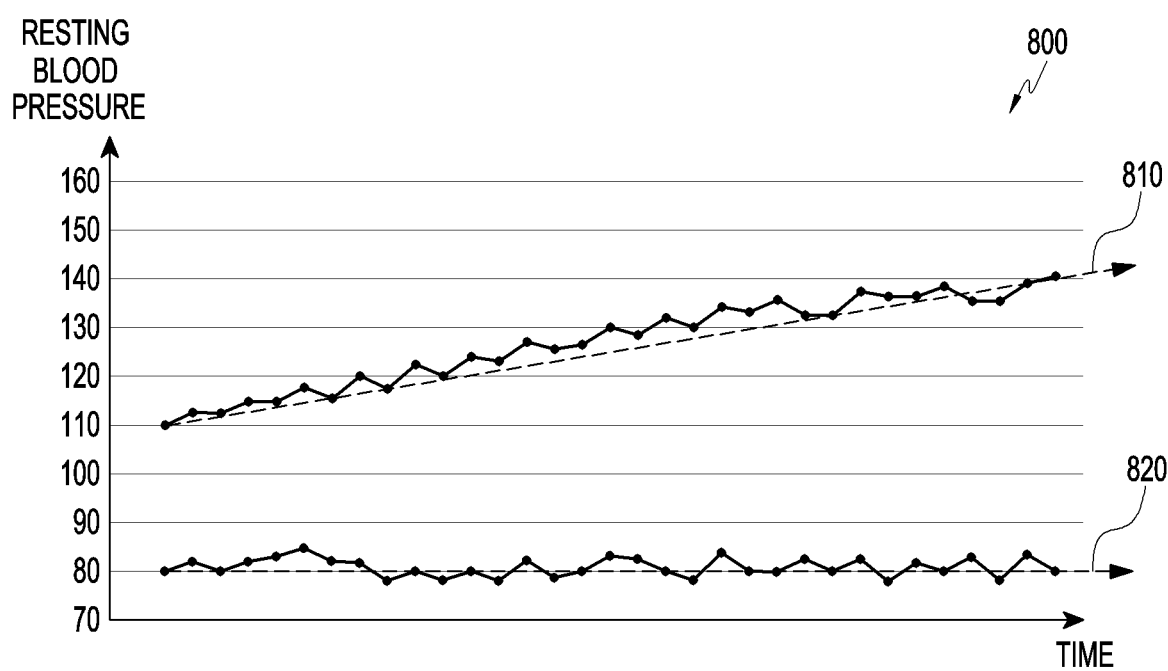
FIGS. 8A, 8B and 8C are views illustrating an example for describing variations in the biometric information measured in a specific circumstance related to a user's body state according to various embodiments.
Figure 8B:
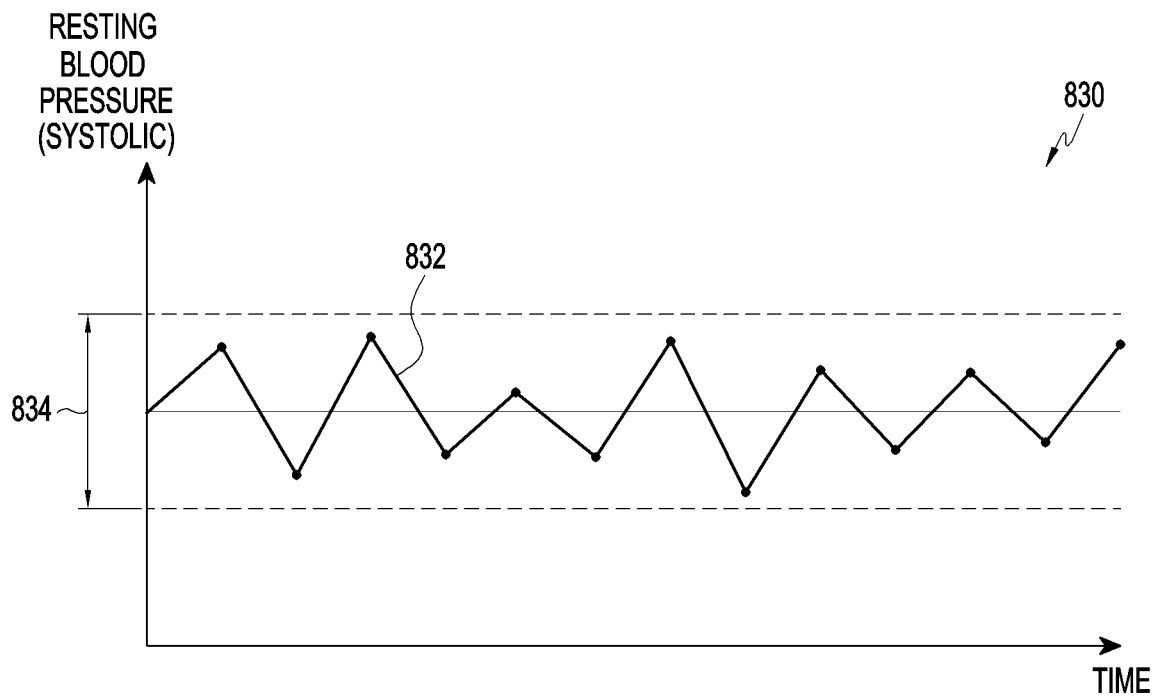
Figure 8C:
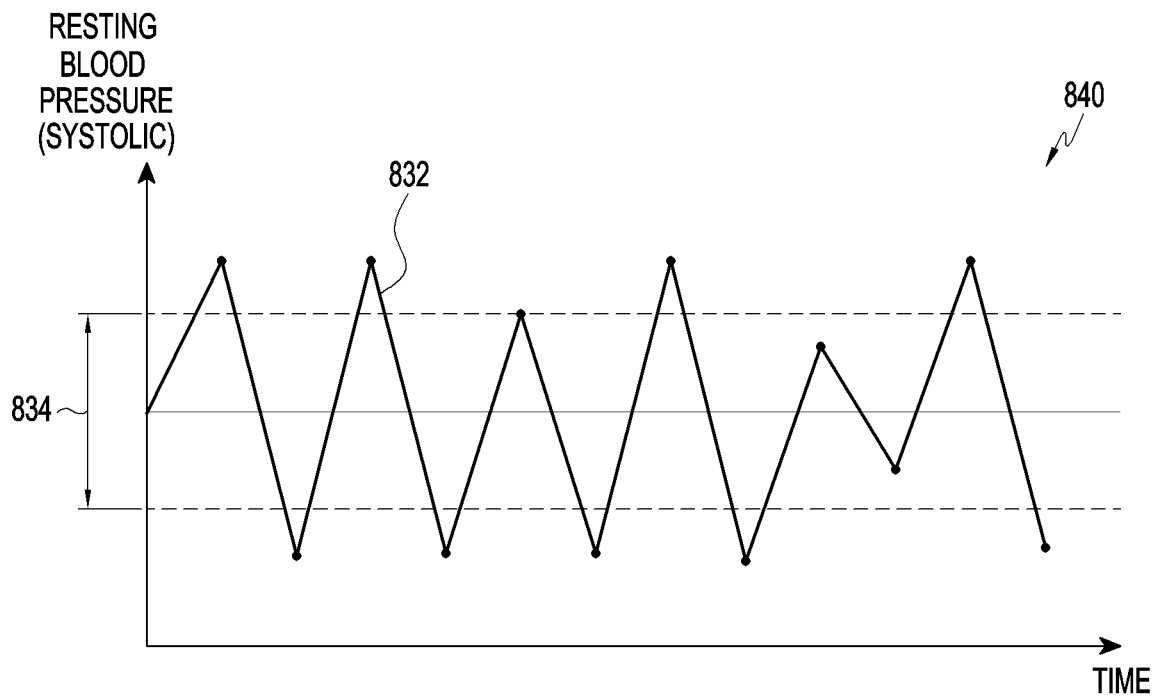

FIGS. 8A to 8C are views illustrating an example for describing variations (e.g., a trend 800) in the biometric information measured in a specific circumstance related to a user's body state according to various embodiments. FIG. 8A illustrates an example trend 800 of biometric information (e.g., blood pressure) measured in the resting state. Referring to FIG. 8A, the trend 800 of biometric information (e.g., blood pressure) during a designated period may have a trend in which a specific factor value (e.g., systolic pressure) increases. According to various embodiments of the disclosure, the electronic device (e.g., the processor 120 of FIG. 2A) may identify the slope of a first trend line 810 and the slope of a second trend line 820. According to various embodiments of the disclosure, the electronic device (e.g., the processor 120 of FIG. 2A) may identify whether the slope of each trend line 810 and 820 exceeds a designated range (e.g., 0% to 3%). According to various embodiments of the disclosure, if the slope of each trend line 810 and 820 exceeds the designated range (e.g., 0% to 3%), the electronic device (e.g., the processor 120 of FIG. 2A) may determine that new reference data needs to be obtained. However, what has been described in connection with FIG. 8 is merely an example, and the designated range may be varied, e.g., −3% to 0%. Further, according to various embodiments of the disclosure, the electronic device (e.g., the processor 120 of FIG. 2A) may determine whether new reference data needs to be obtained based on the trend line (e.g., the second trend line 820) of diastolic pressure.

FIG. 8B illustrates an example diagram 830 when the variation in biometric information (e.g., blood pressure) measured in the resting state falls within a designated range (which may include both when it is not more than a designated value and when it is less than the designated value). According to various embodiments of the disclosure, the electronic device (e.g., the processor 120 of FIG. 2A) may identify whether the variation in biometric information (e.g., the variation in systolic pressure 832) exceeds a designated range 834 with respect to a reference blood pressure (e.g., a preset blood pressure value or the average of blood pressures (e.g., systolic pressure) measured up to a designated time). According to various embodiments of the disclosure, the electronic device (e.g., the processor 120 of FIG. 2A) may identify the variation in biometric information (e.g., blood pressure) based on the standard deviation (or variance) of the blood pressure values computed with respect to, e.g., the reference blood pressure. According to various embodiments of the disclosure, upon identifying the variation in biometric information, such as the diagram 830 of FIG. 8B, the electronic device (e.g., the processor 120 of FIG. 2A) may identify that comparison with new reference data is not needed (e.g., the current reference data is available).

FIG. 8C illustrates an example diagram 840 when the variation in biometric information (e.g., blood pressure) measured in the resting state exceeds a designated range (or is not less than the designated range). According to various embodiments of the disclosure, the electronic device (e.g., the processor 120 of FIG. 2A) may identify whether the variation in biometric information (e.g., the variation in the systolic pressure 832) exceeds a designated range 834 in the same manner as that described above in connection with FIG. 8B. According to various embodiments of the disclosure, if the variation as shown in FIG. 8C is identified, the electronic device (e.g., the processor 120 of FIG. 2A) may identify that comparison with the new reference data is required.

Figure 9A:
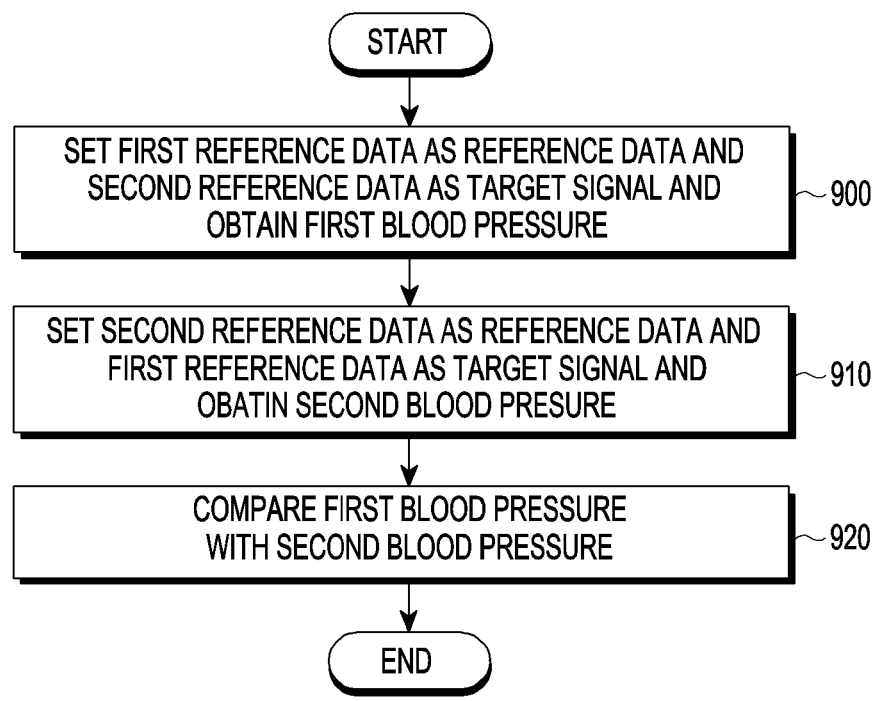
FIGS. 9A and 9B are views illustrating an example method of operating an electronic device according to various embodiments.
Figure 9B:
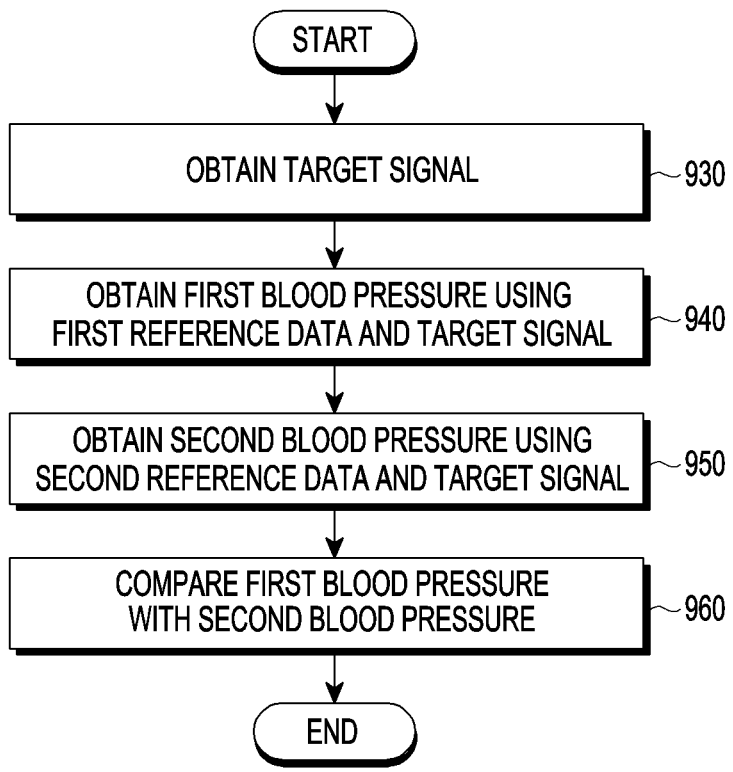

FIGS. 9A and 9B are views illustrating an example method of operating an electronic device according to various embodiments. FIGS. 9A and 9B illustrate various embodiments of comparing a first reference signal included in the first reference data and a second reference signal included in the second reference data in connection with operation 740 of FIG. 7.

Referring to FIG. 9A, according to various embodiments of the disclosure, in the method of operating the electronic device (e.g., the electronic device 101 of FIG. 2A), the electronic device (e.g., the processor 120 of FIG. 2A) may set the first reference data as reference data and the second reference data as a target signal to thereby obtain a first blood pressure in operation 900.

According to various embodiments of the disclosure, in the method of operating the electronic device (e.g., the electronic device 101 of FIG. 2A), the electronic device (e.g., the processor 120 of FIG. 2A) may set the second reference data as the reference data and the first reference data as the target signal to thereby obtain a second blood pressure in operation 910.

According to various embodiments of the disclosure, in the method of operating an electronic device (e.g., the electronic device 101 of FIG. 2A), the electronic device (e.g., the processor 120 of FIG. 2A) may compare the first blood pressure with the second blood pressure in operation 920. According to various embodiments of the disclosure, in operation 920, the electronic device (e.g., the processor 120 of FIG. 2A) may compare at least one blood pressure of the systolic pressure and diastolic pressure. According to various embodiments of the disclosure, if the systolic pressure of the first blood pressure is 130 mmHg, and the systolic pressure of the second blood pressure is 125 mmHg, as an example, the electronic device (e.g., the processor 120 of FIG. 2A) may determine that an error between the blood pressures is 3.84% with respect to the first blood pressure. In this case, if the designated error range is 0% to 3%, the electronic device (e.g., the processor 120 of FIG. 2A) according to various embodiments of the present invention may determine that the designated error range has been exceeded. According to various embodiments of the disclosure, the electronic device (e.g., the processor 120 of FIG. 2A) may determine the error with respect to the second blood pressure. According to various embodiments of the disclosure, the electronic device (e.g., the processor 120 of FIG. 2A) may determine the error with respect to each of the first blood pressure and the second blood pressure. In this case, in operation 750 of FIG. 7, it may be determined whether the result of comparison performed with respect to the larger error value falls within the designated error range.

Referring to FIG. 9B, according to various embodiments of the disclosure, in the method of operating the electronic device (e.g., the electronic device 101 of FIG. 2A), the electronic device (e.g., the processor 120 of FIG. 2A) may obtain a target signal using a biometric sensor (e.g., the biometric sensor 230 of FIG. 2A) in operation 930. According to various embodiments of the disclosure, the target signal may mean a biometric signal (e.g., a PPG signal) obtained from the user to measure the user's current blood pressure.

According to various embodiments of the disclosure, in the method of operating the electronic device (e.g., the electronic device 101 of FIG. 2A), the electronic device (e.g., the processor 120 of FIG. 2A) may obtain the first blood pressure using the first reference data and target signal in operation 940.

According to various embodiments of the disclosure, in the method of operating the electronic device (e.g., the electronic device 101 of FIG. 2A), the electronic device (e.g., the processor 120 of FIG. 2A) may obtain the second blood pressure using the second reference data and target signal in operation 950.

According to various embodiments of the disclosure, in the method of operating an electronic device (e.g., the electronic device 101 of FIG. 2A), the electronic device (e.g., the processor 120 of FIG. 2A) may compare the first blood pressure with the second blood pressure in operation 960. According to various embodiments of the disclosure, in operation 960, the electronic device (e.g., the processor 120 of FIG. 2A) may compare at least one blood pressure of the systolic pressure and diastolic pressure.

Figure 10A:
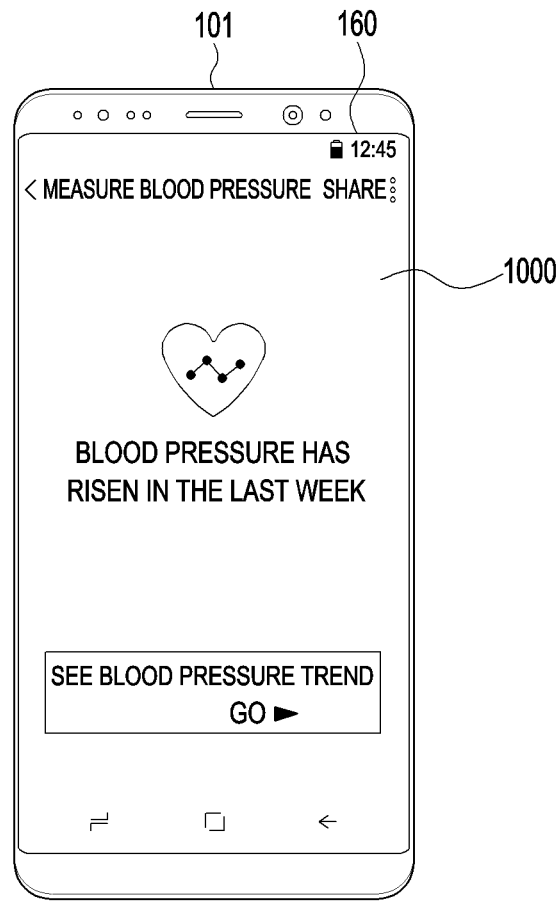
FIGS. 10A, 10B and 10C are views illustrating an example for describing a user interface to provide a trend of the biometric information measured in a specific circumstance related to a user's body state.
Figure 10B:
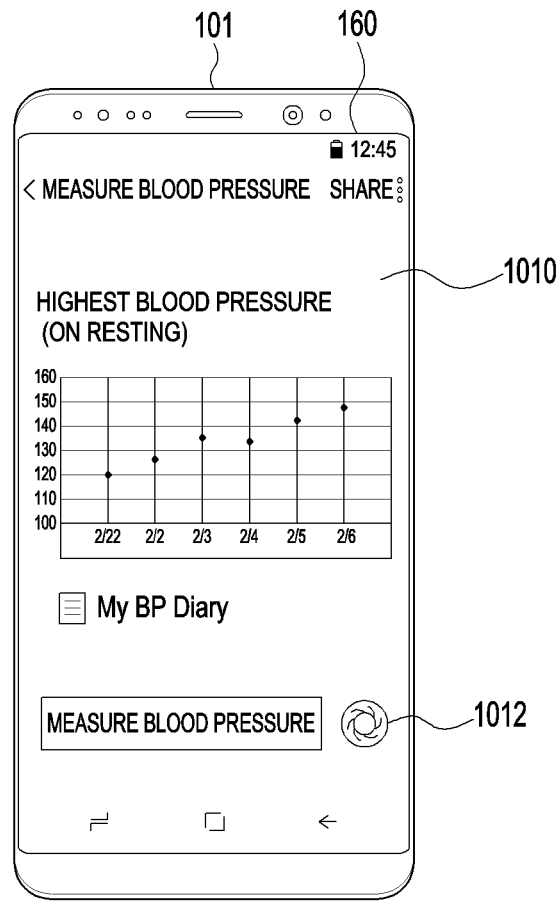
Figure 10C:
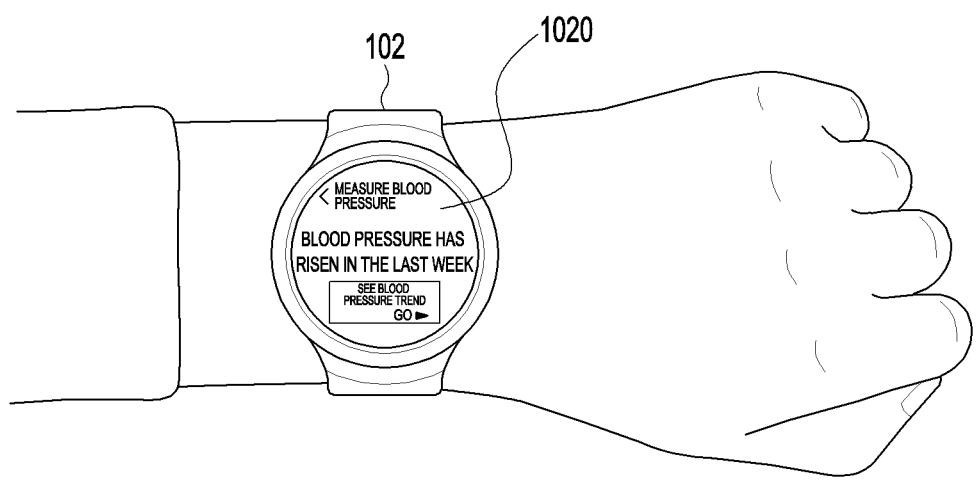

FIGS. 10A to 10C are views illustrating an example for describing a user interface to provide a trend of the biometric information measured in a specific circumstance related to a user's body state.

Referring to FIG. 10A, according to various embodiments of the disclosure, the electronic device (e.g., the processor 120 of FIG. 2A) may provide the user with information regarding the variation trend of biometric information (e.g., blood pressure) during a designated period. According to various embodiments of the disclosure, the electronic device 101 may provide the user with information regarding the variation trend of the biometric information (e.g., blood pressure) measured in a specific circumstance (e.g., the resting state). According to various embodiments of the disclosure, the electronic device 101 may display, on the display device 160 (e.g., the touchscreen display 200 of FIG. 2A), a fourth screen 1000 to provide the user with information regarding the variation trend of the biometric information (e.g., blood pressure) measured in a specific circumstance (e.g., the resting state).

Referring to FIG. 10B, according to various embodiments of the disclosure, the electronic device 101 may display a fifth screen 1010 including information regarding the trend of the biometric information (e.g., blood pressure) measured in a specific circumstance (e.g., the resting state), according to the user's selection input to the fourth screen 1000. According to various embodiments of the disclosure, the electronic device 101 may display the information regarding the variation trend, e.g., in the form of a graph. According to various embodiments of the disclosure, the electronic device 101 may display, on the fifth screen 1010, a graphical object 1012 for switching to a screen for providing the user with breathing guidance. According to various embodiments of the disclosure, upon receiving a selection input (e.g., the user's touch input) to the graphical object 1012, the electronic device 101 may display a screen for providing breathing guidance on the display device 160.

Referring to FIG. 10C, according to various embodiments of the disclosure, the fourth screen 1000 and the fifth screen 1010 may also be displayed on an external electronic device 102 (e.g., a wearable device). FIG. 10C illustrates an example screen 1020 resultant from modifying the fourth screen (e.g., the fourth screen 1000 of FIG. 10B), according to various embodiments of the disclosure, to be suited for the external electronic device 102 (e.g., a wearable device).

Figure 11:
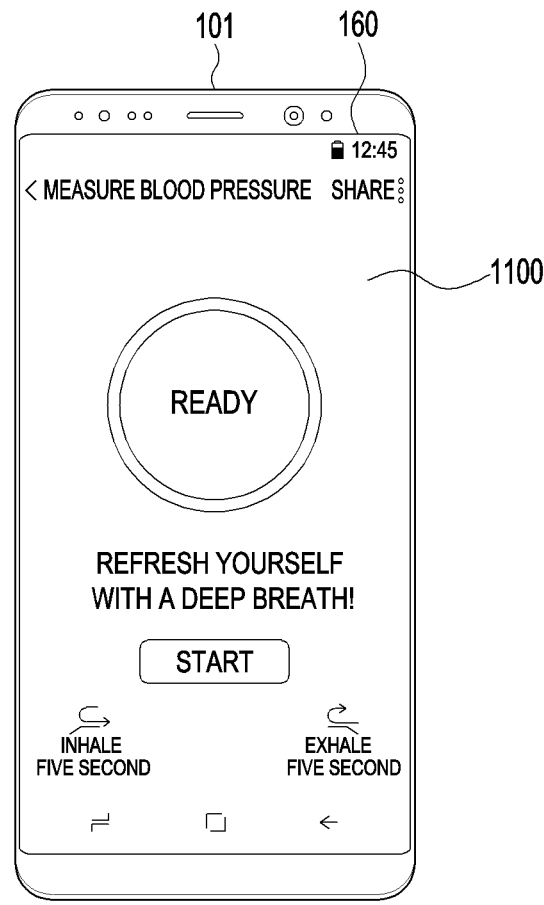
FIG. 11 is a view illustrating an example for describing a user interface to provide a guidance for a user's breathing based on obtained biometric information, according to various embodiments.

FIG. 11 is a view illustrating an example for describing a user interface to provide a guidance for a user's breathing based on obtained biometric information, according to various embodiments.

Referring to FIG. 11, according to various embodiments of the disclosure, the electronic device 101 (e.g., the processor 120 of FIG. 2A) may provide the user with breathing guidance according to the variation trend of the biometric information (e.g., blood pressure) measured in a specific circumstance (e.g., the resting state). According to various embodiments of the disclosure, the electronic device 101 may display a sixth screen 1100, including breathing guidance (e.g., "inhale five seconds"), on the display device 160 (e.g., the touchscreen display 200 of FIG. 2A). According to various embodiments of the disclosure, the electronic device 101 may display the sixth screen 1100 on the display device 160 (e.g., the touchscreen display 200 of FIG. 2A) according to a selection input (e.g., the user's touch input) on the user interface (e.g., the graphical object 1012 of FIG. 10B) displayed on a designated screen (e.g., the fifth screen 1010 of FIG. 10B). According to various embodiments of the disclosure, if the biometric information (e.g., blood pressure) measured in a specific circumstance has a trend of increasing, the electronic device 101 may provide a guidance (e.g., "inhale ten seconds") for leading to slow breathing.

Figure 12A:
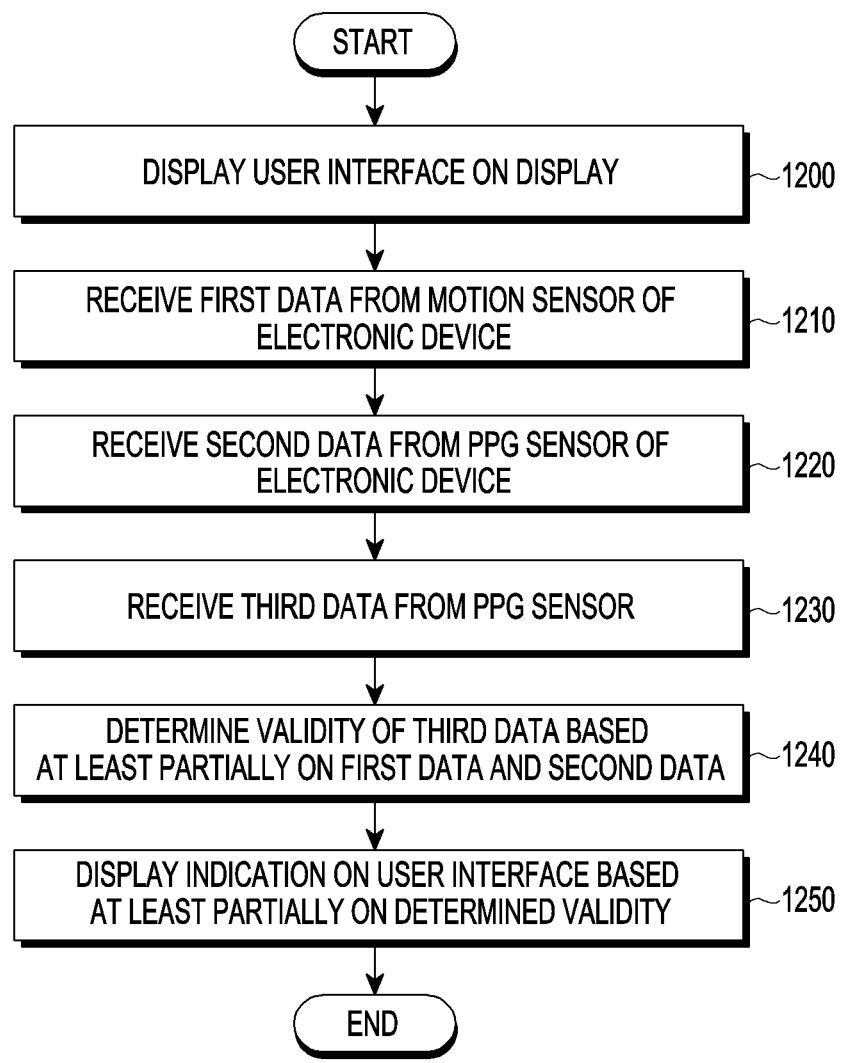
FIGS. 12A and 12B are views illustrating an example method of operating an electronic device according to various embodiments.
Figure 12B:
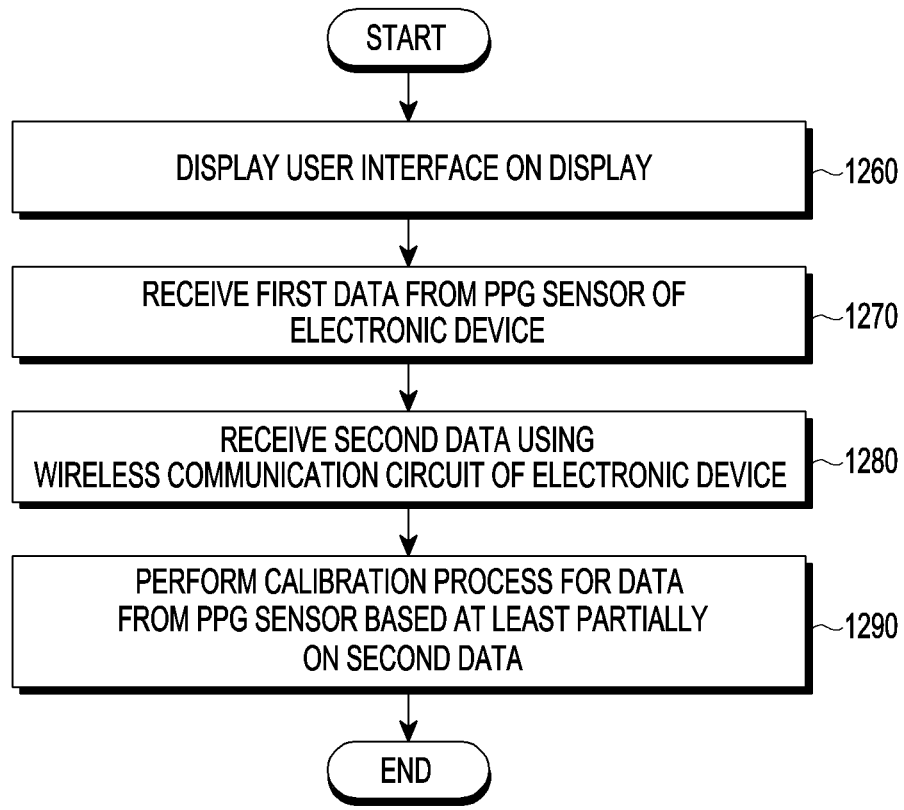

FIGS. 12A and 12B are views illustrating an example method of operating an electronic device according to various embodiments.

Referring to FIG. 12A, according to various embodiments of the disclosure, in the electronic device (e.g., the electronic device 101 of FIG. 2A), the electronic device (e.g., the processor 120 of FIG. 2A) may display a user interface in operation 1200.

According to various embodiments of the disclosure, in the electronic device (e.g., the electronic device 101 of FIG. 2A), the electronic device (e.g., the processor 120 of FIG. 2A) may receive first data from the motion sensor (e.g., the motion sensor 220 of FIG. 2A) of the electronic device in operation 1210.

According to various embodiments of the disclosure, in the electronic device (e.g., the electronic device 101 of FIG. 2A), the electronic device (e.g., the processor 120 of FIG. 2A) may receive second data (e.g., heartrate and/or stress level) from the PPG sensor (e.g., the biometric sensor 230 of FIG. 2A) of the electronic device in operation 1220.

According to various embodiments of the disclosure, in the electronic device 101, the electronic device (e.g., the processor 120 of FIG. 2A) may receive third data (e.g., blood pressure) from the PPG sensor (e.g., the biometric sensor of FIG. 2A) in operation 1230. According to various embodiments of the disclosure, the second data and third data may include data obtained (or identified) from the same PPG signal. According to various embodiments of the disclosure, the second data and third data may include data obtained from each of different PPG signals.

According to various embodiments of the disclosure, in the electronic device 101, the electronic device (e.g., the processor 120 of FIG. 2A) may determine the validity of the third data based at least partially on the first data and the second data in operation 1240.

According to various embodiments, in the electronic device 101, the electronic device (e.g., the processor 120 of FIG. 2A) may display an indication on the user interface based at least partially on the determined validity in operation 1250.

Referring to FIG. 12B, according to various embodiments of the disclosure, in the electronic device 101, the electronic device (e.g., the processor 120 of FIG. 2A) may display the user interface in operation 1260.

According to various embodiments of the disclosure, in the electronic device 101, the electronic device (e.g., the processor 120 of FIG. 2A) may receive the first data from the PPG sensor (e.g., the biometric sensor of FIG. 2A) of the electronic device in operation 1270.

According to various embodiments of the disclosure, in the electronic device 101, the electronic device (e.g., the processor 120 of FIG. 2A) may receive the second data using the wireless communication circuit of the electronic device in operation 1280.

According to various embodiments of the disclosure, in the electronic device 101, the electronic device (e.g., the processor 120 of FIG. 2A) may perform a calibration process for data from the PPG sensor (e.g., the biometric sensor of FIG. 2A) based at least partially on the second data in operation 1290.

According to various embodiments of the disclosure, an electronic device (e.g., the electronic device 101 of FIG. 1) may comprise a housing, a touchscreen display (e.g., the display device 160 of FIG. 1) exposed through a first portion of the housing, a motion sensor (e.g., the sensor module 176 of FIG. 1) disposed inside the housing, a photoplethysmogram (PPG) sensor (e.g., the sensor module 176 of FIG. 1) disposed in a second portion of the housing, a wireless communication circuit (e.g., the communication module 190 of FIG. 1), a processor (e.g., the processor 120 of FIG. 1) operatively connected with the display, the motion sensor, the PPG sensor, and the wireless communication circuit, and a memory (e.g., the memory 130 of FIG. 1) operatively connected with the processor, wherein the memory stores instructions executed to enable the processor to display a user interface on the display, the user interface providing a guidance for blood pressure measurement, receive first data from the motion sensor and second data from the PPG sensor, receive third data from the PPG sensor, determine a validity of the third data based at least partially on the first data and the second data, and display an indication on the user interface based at least partially on the determined validity.

According to various embodiments of the disclosure, the PPG sensor may include a light emitting module including at least one LED and a light receiving module at least one photo diode and may be configured to generate PPG data using the at least one LED.

According to various embodiments of the disclosure, the motion sensor may include an acceleration sensor, and the first data may include acceleration data of the electronic device, obtained by the acceleration sensor.

According to various embodiments of the disclosure, the second data may include information about a user's heartrate and stress level identified based on a PPG signal obtained by the PPG sensor.

According to various embodiments of the disclosure, the instructions may further include an instruction to enable the processor to determine the validity of the third data based on acceleration information about the electronic device obtained based on the first data and information regarding a user's heartrate or stress level, obtained based on the second data.

According to various embodiments of the disclosure, the third data may include a PPG signal for identifying a user's blood pressure, obtained by the PPG sensor. The instruction to enable the processor to determine the validity of the third data further may include an instruction to enable the processor to, when the user's activity state is determined to be a resting state based at least partially on the first data and the second data, determine that the third data is valid data.

According to various embodiments of the disclosure, the indication may include an indication for guiding at least one of a user's breathing volume and breathing time upon determining that the user's state determined based at least partially on the first data and the second data is a non-resting state.

According to various embodiments of the disclosure, the instructions may further include an instruction to enable PPI information to be obtained using a PPG signal obtained by the PPG sensor and an instruction to enable the stress level to be determined based on the obtained PPI information.

According to various embodiments of the disclosure, the instructions may further include an instruction to enable the processor to receive fifth data from the PPG sensor, based on at least part of a designated number of times and a designated period.

According to various embodiments of the disclosure, the instructions may further include an instruction to enable the processor to measure the user's blood pressure based at least partially on fifth data received from the PPG sensor and an instruction to enable the processor to determine whether the user's blood pressure is increased, decreased, or maintained a designated number of times or during a designated period based on the measured blood pressure.

According to various embodiments of the disclosure, the instructions may further include an instruction to enable the processor to, upon determining that the user's blood pressure is increased or decreased the designated number of times or during the designated period, obtain sixth data using the wireless communication circuit.

According to various embodiments of the disclosure, the instructions may further include an instruction to enable the processor to set a first PPG signal corresponding to the fourth data as a reference signal for measuring the user's blood pressure and a second PPG signal corresponding to the sixth data as a target signal for measuring the user's blood pressure to measure the user's first blood pressure and an instruction to enable the processor to set the second PPG signal as the reference signal and the first PPG signal as the target signal to measure the user's second blood pressure.

According to various embodiments of the disclosure, the instructions may further include an instruction to enable the processor to determine whether a difference between a systolic pressure corresponding to the first blood pressure and a systolic pressure corresponding to the second blood pressure exceeds a designated error range and an instruction to enable the processor to, when the difference exceeds the designated error range, update the first PPG signal with the second PPG signal.

According to various embodiments of the disclosure, the instructions may further include an instruction to enable the processor to determine whether a difference between a systolic pressure corresponding to the first blood pressure and a systolic pressure corresponding to the second blood pressure exceeds a designated error range and an instruction to enable the processor to, when the difference is less than the designated error range, display an indication for a notification for a variation in the user's blood pressure on the touchscreen display.

According to various embodiments of the disclosure, the fourth data may include data generated at a substantially different time from the sixth data.

According to various embodiments of the disclosure, an electronic device may comprise a housing, a touchscreen display exposed through a first portion of the housing, a motion sensor disposed inside the housing, an optical blood pressure sensor disposed in a second portion of the housing, a PPG sensor disposed, adjacent to the blood pressure sensor, in a third portion of the housing, a wireless communication circuit, a processor operatively connected with the display, the motion sensor, the optical blood pressure sensor, the PPG sensor, and the wireless communication circuit, and a memory operatively connected with the processor, wherein the memory stores instructions executed to enable the processor to display a user interface on the display, the user interface providing a guidance for blood pressure measurement, receive first data from the motion sensor and second data from the PPG sensor, receive third data from the blood pressure sensor, determine a validity of the third data based at least partially on the first data and the second data, and display an indication on the user interface based at least partially on the determined validity.

According to various embodiments of the disclosure, an optical sensor may be further included. The blood pressure sensor may include a first LED and be configured to generate blood pressure data using the optical sensor. The PPG sensor may include a second LED and be configured to generate PPG data (or PPG signal) using the optical sensor.

According to various embodiments of the disclosure, the instructions may further include an instruction to enable the processor to determine the validity of the third data based on acceleration information about the electronic device obtained based on the first data and information regarding a user's heartrate or stress level, obtained based on the second data.

According to various embodiments of the disclosure, an electronic device may comprise a housing, a touchscreen display exposed through a first portion of the housing, a motion sensor disposed inside the housing, a photoplethysmogram (PPG) sensor disposed in a second portion of the housing, a wireless communication circuit, a processor operatively connected with the display, the motion sensor, the PPG sensor, and the wireless communication circuit, and a memory operatively connected with the processor, wherein the memory stores instructions executed to enable the processor to display a user interface on the display, the user interface providing a guidance for blood pressure measurement, receive first data from the PPG sensor, receive second data using the wireless communication circuit, the second data generated substantially simultaneously with the first data, and perform a calibration process on data from the PPG sensor based at least partially on the second data.

According to various embodiments of the disclosure, the instruction to enable it to be determined whether the difference between the systolic pressure corresponding to the first blood pressure and the systolic pressure corresponding to the second blood pressure exceeds the designated error range may include an instruction to enable it to be determined whether it exceeds the designated error range based on the variance or standard deviation of the systolic pressure corresponding to the first blood pressure and the systolic pressure corresponding to the second blood pressure.

The electronic device according to various embodiments may be one of various types of electronic devices. The electronic devices may include, for example, a portable communication device (e.g., a smart phone), a computer device, a portable multimedia device, a portable medical device, a camera, a wearable device, or a home appliance. According to an embodiment of the present invention, the electronic device is not limited to the above-listed embodiments.

It should be appreciated that various embodiments of the present disclosure and the terms used therein are not intended to limit the technological features set forth herein to particular embodiments and include various changes, equivalents, or replacements for a corresponding embodiment. With regard to the description of the drawings, similar reference numerals may be used to refer to similar or related elements. It is to be understood that a singular form of a noun corresponding to an item may include one or more of the things, unless the relevant context clearly indicates otherwise. As used herein, each of such phrases as "A or B," "at least one of A and B," "at least one of A or B," "A, B, or C," "at least one of A, B, and C," and "at least one of A, B, or C," may include all possible combinations of the items enumerated together in a corresponding one of the phrases. As used herein, such terms as "1st" and "2nd," or "first" and "second" may be used to simply distinguish a corresponding component from another, and does not limit the components in other aspect (e.g., importance or order). It is to be understood that if an element (e.g., a first element) is referred to, with or without the term "operatively" or "communicatively", as "coupled with," "coupled to," "connected with," or "connected to" another element (e.g., a second element), it means that the element may be coupled with the other element directly (e.g., wiredly), wirelessly, or via a third element.

As used herein, the term "module" may include a unit implemented in hardware, software, or firmware, and may interchangeably be used with other terms, for example, "logic," "logic block," "part," or "circuitry". A module may be a single integral component, or a minimum unit or part thereof, adapted to perform one or more functions. For example, according to an embodiment, the module may be implemented in a form of an application-specific integrated circuit (ASIC).

Various embodiments as set forth herein may be implemented as software (e.g., the program 140) including one or more instructions that are stored in a storage medium (e.g., internal memory 136 or external memory 138) that is readable by a machine (e.g., the electronic device 101). For example, a processor (e.g., the processor 120) of the machine (e.g., the electronic device 101) may invoke at least one of the one or more instructions stored in the storage medium, and execute it, with or without using one or more other components under the control of the processor. This allows the machine to be operated to perform at least one function according to the at least one instruction invoked. The one or more instructions may include a code generated by a complier or a code executable by an interpreter. The machine-readable storage medium may be provided in the form of a non-transitory storage medium. Wherein, the term "non-transitory" simply means that the storage medium is a tangible device, and does not include a signal (e.g., an electromagnetic wave), but this term does not differentiate between where data is semi-permanently stored in the storage medium and where the data is temporarily stored in the storage medium.

According to an embodiment, a method according to various embodiments of the disclosure may be included and provided in a computer program product. The computer program products may be traded as commodities between sellers and buyers. The computer program product may be distributed in the form of a machine-readable storage medium (e.g., compact disc read only memory (CD-ROM)), or be distributed (e.g., downloaded or uploaded) online via an application store (e.g., Play Store™), or between two user devices (e.g., smart phones) directly. If distributed online, at least part of the computer program product may be temporarily generated or at least temporarily stored in the machine-readable storage medium, such as memory of the manufacturer's server, a server of the application store, or a relay server.

According to various embodiments, each component (e.g., a module or a program) of the above-described components may include a single entity or multiple entities. According to various embodiments, one or more of the above-described components may be omitted, or one or more other components may be added. Alternatively or additionally, a plurality of components (e.g., modules or programs) may be integrated into a single component. In such a case, according to various embodiments, the integrated component may still perform one or more functions of each of the plurality of components in the same or similar manner as they are performed by a corresponding one of the plurality of components before the integration. According to various embodiments, operations performed by the module, the program, or another component may be carried out sequentially, in parallel, repeatedly, or heuristically, or one or more of the operations may be executed in a different order or omitted, or one or more other operations may be added.

What is claimed is:

1. An electronic device, comprising:
a display;
a motion sensor;
a photoplethysmogram (PPG) sensor;
a wireless communication circuit;
a processor operatively connected with the display, the motion sensor and the PPG sensor; and
a memory operatively connected with the processor, wherein the memory stores instructions configured to, when executed, enable the processor to:
obtain first data from the motion sensor and second data from the PPG sensor,
identify whether a user's activity state is resting state based on the first data and the second data, when the first data does not exceed a first specified range and the second data does not exceed a second specified range, and
when the user's activity state is the resting state, obtain blood pressure data from the PPG sensor,
identify whether an amount of change in the blood pressure data exceeds a third specified range,
obtain second reference data, from an external electronic device connected to the electronic device using the wireless communication circuit, for updating first reference data when the amount of change in the blood pressure data exceeds the third specified range,
compare the first reference data and the second reference data,
identify whether a result of comparison between the first reference data and the second reference data exceeds a fourth specified range,
when the result of the comparison exceeds the fourth specified range, update the first reference data to the second reference data, and
based on the second reference data, perform a calibration process.

2. The electronic device of claim 1, wherein the instructions further include an instruction to enable the processor to, from the PPG sensor, obtain PPG data based on a specified number of times and a specified time period.

3. The electronic device of claim 2, wherein the instructions further include an instruction to enable the processor to measure the blood pressure data of the user based on the PPG data obtained from the PPG sensor.

4. The electronic device of claim 1, wherein the instructions further include an instruction to enable the processor to identify whether the amount of change in the blood pressure data exceeds the third specified range based on whether a standard deviation of the blood pressure data of a specified period exceeds a specified value.

5. The electronic device of claim 1, wherein the PPG sensor includes a light emitting module including at least one LED and a light receiving module including at least one photodiode, and configured to generate PPG data using the at least one LED.

6. A method for controlling an electronic device, comprising:
obtaining first data from a motion sensor of the electronic device and second data from a PPG sensor of the electronic device,
identifying whether a user's activity state is resting state based on the first data and the second data, when the first data does not exceed a first specified range and the second data does not exceed a second specified range, and
when the user's activity state is the resting state, obtaining blood pressure data from the PPG sensor,
identifying whether an amount of change in the blood pressure data exceeds a third specified range,
obtaining second reference data, from an external electronic device connected to the electronic device using a wireless communication circuit of the electronic device, for updating first reference data when the amount of change in the blood pressure data exceeds the third specified range,
comparing the first reference data and the second reference data,
identifying whether a result of comparison exceeds a fourth specified range,
when the result of the comparison exceeds the fourth specified range, updating the first reference data to the second reference data, and
based on the second reference data, performing a calibration process.

7. The method of claim 6, further comprising, from a photoplethysmogram (PPG) sensor of the electronic device, obtaining PPG data based on a specified number of times and a specified time period.

8. The method of claim 7, further comprising measuring the blood pressure data of the user based on the PPG data obtained from the PPG sensor.

9. The method of claim 6, wherein the identifying whether the amount of change in the blood pressure data exceeds the third specified range includes identifying whether the amount of change in the blood pressure exceeds the third specified range based on whether a standard deviation of blood pressure data of a specified period exceeds a specified value.

10. The method of claim 6, wherein a photoplethysmogram (PPG) sensor of the electronic device includes a light emitting module including at least one LED and a light receiving module including at least one photodiode, and configured to generate PPG data using the at least one LED.

* * * * *